United States Patent
Li et al.

(10) Patent No.: US 11,111,492 B2
(45) Date of Patent: Sep. 7, 2021

(54) GENOME ENGINEERING METHODS USING A CYTOSINE-SPECIFIC CAS9

(71) Applicant: Florida State University Research Foundation, Inc., Tallahassee, FL (US)

(72) Inventors: Hong Li, Tallahassee, FL (US); Martin Tsui, Tallahassee, FL (US); Travis Hand, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 362 days.

(21) Appl. No.: 15/913,444

(22) Filed: Mar. 6, 2018

(65) Prior Publication Data

US 2018/0265864 A1  Sep. 20, 2018

Related U.S. Application Data

(60) Provisional application No. 62/467,577, filed on Mar. 6, 2017.

(51) Int. Cl.
*C12N 15/11* (2006.01)
*C12N 9/22* (2006.01)

(52) U.S. Cl.
CPC .............. *C12N 15/11* (2013.01); *C12N 9/22* (2013.01); *C12N 15/111* (2013.01); *C12N 2310/20* (2017.05); *C12N 2800/80* (2013.01)

(58) Field of Classification Search
CPC ...... C12N 2310/20; C12N 15/11; C12N 9/22; C12N 15/111; C12N 2800/80
See application file for complete search history.

(56) References Cited

U.S. PATENT DOCUMENTS

2019/0048415 A1* 2/2019 Walter ................. C12Q 1/6832
2019/0249200 A1* 8/2019 Seebeck ............... C12N 15/102

OTHER PUBLICATIONS

Loder Dissertation, (North Carolina State University, published in 2016) (Year: 2016).*
Tsui etal (ACS Syn Biol 2017, vol. 6, pp. 1103-0003, published Mar. 9, 2017). (Year: 2017).*
Tsui Dissertation (2017). (Year: 2017).*
Chylinski et al (RNA Biology, 2013). (Year: 2013).*
Hou et al., "Efficient Genome Engineering in Human Pluripotent Cells Using Cas9 from neisseria Meningitidis," PNAS, 2013, 110(39):15644-15649.
Jiang et al., "RNA-Guided Editing of Bacterial Genomes Using CRISPR-Cas Systems," Nature Biotechnology, 2013, 31(3):233-241.
Jinek et al., "A Programmable Dual-RNA-Guided Endonuclease in Adaptive Bacterial Immunity," Science, 2012, 337:816-821.
Ran et al., "In Vivo Genome Editing Using *Staphylococcus aureus* Cas9," Nature, 2015, 520:186-203.

* cited by examiner

*Primary Examiner* — Catherine S Hibbert
(74) *Attorney, Agent, or Firm* — Eversheds Sutherland (US) LLP

(57) ABSTRACT

Described herein are methods and compositions for rapid and precise genome editing at any desired genomic position in almost all cells and organisms. The methods utilize a cytosine-specific Cas9 endonuclease and are suitable for applications requiring targeting cytosine adjacent DNA. The methods generally include introducing a cytosine-specific Cas9 endonuclease, a single guide RNA, and optionally a DNA repair template that is utilized in either non-homologous end joining or homology directed repair. The methods can be used to effect gene knockout, gene knockdown, gene substitution, or gene introduction in cells and organisms.

16 Claims, 23 Drawing Sheets
(11 of 23 Drawing Sheet(s) Filed in Color)

Specification includes a Sequence Listing.

Plasmid Protospacer Mutants

|  | Protospacer | PAM |
|---|---|---|
| pPSWT | 5' ...GGTAggatggcaagatcctggtat | ACACC... 3' |
| pPST(-1)G | 5' ...GGTAggatggcaagatcctggtag | ACACC... 3' |
| pPSG(-4)A | 5' ...GGTAggatggcaagatcctgatat | ACACC... 3' |
| pPSG(-8)T | 5' ...GGTAggatggcaagattctggtat | ACACC... 3' |
| pPSC(-20)A | 5' ...GGTAagatggcaagatcctggtat | ACACC... 3' |
| pPSG(-19,-20)A | 5' ...GGTAaaatggcaagatcctggtat | ACACC... 3' |

FIG. 5A

```
                      Randamized Bases
Close 01  CTCTTCCGATCTGGTATTCCCACTAAGAAACCATTATTCATCATGACATTAACCTATAAA
Close 02  --CTCTTCCGATCTTATCCCCGTAAGAAACCATTATTCATCATGACATTAACCTATAAA*
Close 03  --CTCTTCCGATCTTATACCCCGTAAGAAACCATTATTCATCATGACATTAACCTATAAA*
Close 04  --CTCTTCCGATCTTATACCCCGTAAGAAACCATTATTCATCATGACATTAACCTATAAA*
Close 05  --CTCTTCCGATCTTATACACCCGTAAGAAACCATTATTCATCATGACATTAACCTATAAA*
Close 06  --CTCTTCCGATCTTATACACCCTAAGAAACCATTATTCATCATGACATTAACCTATAAA*
Close 07  --CTCTTCCGATCTTATACACCCTAAGAAACCATTATTCATCATGACATTAACCTATAAA*
Close 08  --CTCTTCCGATCTTATACACCCTAAGAAACCATTATTCATCATGACATTAACCTATAAA*
Close 09  --CTCTTCCGATCTTATTCCCAGTAAGAAACCATTATTCATCATGACATTAACCTATAAA*
Close 10  --CTCTTCCGATCTTATTTCCAGTAAGAAACCATTATTCATCATGACATTAACCTATAAA*
Close 11  --CTCTTCCGATCTTATTACCCACTAAGAAACCATTATTCATCATGACATTAACCTATAAA*
Close 12  --CTCTTCCGATCTTATTACCCACTAAGAAACCATTATTCATCATGACATTAACCTATAAA*
Close 13  --CTCTTCCGATCTTATCAACCCATAAGAAACCATTATTCATCATGACATTAACCTATAAA*
Close 14  --CTCTTCCGATCTTATCTACCTATAAGAAACCATTATTCATCATGACATTAACCTATAAA*
Close 15  --CTCTTCCGATCTTATCCACCTTTAAGAAACCATTATTCATCATGACATTAACCTATAAA*
Close 16  --CTCTTCCGATCTTATCCACCTTTAAGAAACCATTATTCATCATGACATTAACCTATAAA*
Close 17  --CTCTTCCGATCTTATCCCATTAAGAAACCATTATTCATCATGACATTAACCTATAAA*
Close 18  --CTCTTCCGATCTTATCCCCATAAGAAACCATTATTCATCATGACATTAACCTATAAA*
```

FIG. 7C

PAM

WT2       5-GGTAggatggcaagatcctggtatGATCCTGTGC[FAM]-3
          3-CCATcctaccgttctaggaccataCTAGGACACG-5*

PAM-G4.5C*  5-GGTAggatggcaagatcctggtatGATCCTGTGC[FAM]-3
            3-CCATcctaccgttctaggaccataCTACCACACG-5*

GENOME ENGINEERING METHODS USING A CYTOSINE-SPECIFIC CAS9

REFERENCES TO RELATED APPLICATIONS

This application claims priority to U.S. Provisional Patent Application No. 62/467,577, filed Mar. 6, 2017, which is incorporated herein by reference.

STATEMENT AS TO FEDERALLY SPONSORED RESEARCH

This work was supported by American Heart Association predoctoral fellowship 15PRE25330004 and by NIH grant R01 GM099604.

SEQUENCE LISTING

The instant application contains a Sequence Listing which has been submitted electronically in ASCII format and is hereby incorporated by reference in its entirety. Said ASCII copy, created on May 1, 2018, is named 19585-0281_SL.txt and is 24,827 bytes in size.

BACKGROUND

Cas9 is an RNA-guided DNA cleavage enzyme utilized by some bacteria to defend against invading species, such as bacteriophages, through the Clustered Regularly Interspaced Short Palindromic Repeats (CRISPR)-mediated pathway. A functional Cas9 is comprised of a polypeptide and two short RNAs, a CRISPR RNA (crRNA) and a trans-activating crRNA (tracrRNA). In previously characterized Cas9s, the crRNA and tracrRNA could be covalently linked into a chimeric RNA called single guide RNA (sgRNA) with no loss of function. The ability of Cas9 to target any double stranded DNA (dsDNA) for cleavage using customizable guides has enabled development of multiple Cas9-based biotechnologies. Introducing cells with Cas9 and a sgRNA results in site-specific double-stranded breaks (DSB) that trigger either non-homologous end joining (NHEJ) or homology directed repair (HDR). These DNA repair processes can be utilized to either disrupt protein-encoding genes (gene knockout and gene knockdown) or to substitute a gene of choice using a desired DNA template through homologous recombination (gene editing). In addition, catalytically inactive Cas9 (dCas9) has been applied in transcriptional regulation and other applications through its programmable binding to specific DNA elements. The power of the CRISPR-Cas9 effector nuclease as a genome-editing tool has been demonstrated in multiple organisms and cell types. However, currently available Cas9s, both natural and engineered, still lack diversity in substrate selection. Furthermore, these Cas9s continue to show off-target cleavage activity. Broadening the choice of Cas9s while improving Cas9 specificity is a major goal in the field of Cas9-based biotechnology.

Cas9 requires two elements within the DNA target for cleavage: 1) an 18-24 base pairs (protospacer) complementary to the guide region of the sgRNA and 2) a Cas9-specific 3-8 nucleotides (nts) adjacent to the protospacer known as PAM (Protospacer Adjacent Motif). Structural and fluorescence studies suggest that specific recognition of the short PAM nucleotides by Cas9 leads to unwinding of the protospacer and formation of a structural motif called the R-loop in which the sgRNA base pairs with the targeting strand of the protospacer. Subsequently, the HNH- and RuvC-like nuclease domains of Cas9 reposition to the targeting and the non-targeting strand of the dsDNA, respectively, to generate a DSB. In most CRISPR-Cas9 systems, the absence of a PAM consensus from self DNA, such as the CRISPR repeats, prevents self-destruction. Notably, though both the complementarity to sgRNA and the PAM of a DNA substrate are required for its cleavage by Cas9, low-level activities have been observed for DNA containing deviations from these elements (the protospacer, in particular), leading to cleavage of unintended targets. The processes of Cas9 assembly, dsDNA unwinding, and interaction with protospacers and PAM all contribute to the control of substrate cleavage that, if understood, may be harnessed for improvement of Cas9-based biotechnology.

Most of the well-characterized Cas9s require PAM sequences comprised of guanine nucleotide(s) located 2-3 bases from the 3' end of the non-targeting strand of the protospacer. Despite low sequence homology of the PAM interacting domain (PID) among the known Cas9s, crystal structures of *Streptococcus pyogenes* (Spy) Cas9 (type II-A, 5'-NGG-3'), *Staphylococcus aureus* (Sa) Cas9 (type II-A, 5'-NNGRRT-3'), and *Francisella novicida* (Fn) Cas9 (type II-B, 5'-NGG-3') bound to their DNA substrates revealed a similar mechanism of PAM recognition that involves guanine base-specific contacts primarily by arginine residues. Mutation of these arginine residues reduced Cas9 activity or altered the PAM sequence recognized by specific Cas9 enzymes. Given the wide sequence variation in PID, it is possible that some Cas9s have evolved to either position arginine differently or rely on other polar residues in accommodating different PAMs than currently known. Identification and characterization of additional PAM-Cas9 interactions will contribute to the knowledge of Cas9 activity control.

Previous studies show that recognition of the protospacer by Cas9 plays an important role in substrate cleavage. The guide region of the sgRNA (spacer), typically 20-nt in length, serves as the key component in substrate recognition of the Cas9 enzyme by base pairing with the targeting strand of the protospacer. Both the length and sequence of the spacer impact the enzyme efficiency as well as specificity. Cas9 uses its large nucleic acid recognition (REC) domain to nearly enwrap the DNA-spacer heteroduplex. However, the REC-mediated heteroduplex recognition has moderate fidelity, as disruption of base pairing between the spacer of sgRNA and the targeting strand at both the PAM-distal and PAM-adjacent ends is tolerated by Cas9 both in vitro and in vivo. Tolerance of mismatched DNA-spacer by Cas9 is a source of unwanted off-target cleavage in cells. Efforts to increase specificity of the widely used SpyCas9 were made by engineering regions in both sgRNA and Cas9, by reducing its expression level, or by employing double sgRNA with Cas9 nickase. Furthermore, reducing the heteroduplex base pairs from 20 to 17-18-nts was found to enhance SpyCas9's ability to discriminate mismatches. Recently, mutations of positively charged residues within the heteroduplex binding REC and nuclease domains were shown to also increase the specificity of SpyCas9. Note that these engineering strategies led to reduced Cas9 non-specific binding affinity for the substrate, raising the possibility that reduction of enzyme activity could in general benefit specific cleavage by Cas9.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A (Top) shows CRISPR locus in *A.cellulolyticus* 11B and the sequences of CRISPR RNA (crRNA) and trans-activating crRNA (tracrRNA). Black rectangles (R), indicate consensus direct repeat sequence and colored diamonds (S) indicate spacer sequences. The red arrow indicates the putative transcription direction for tracrRNA. FIG. 1A (Bottom) shows a schematic representation of R-loop formation between the dsDNA target and the constructed single guide RNA (sgRNA). The guide region of sgRNA (or spacer) is shown in red and base pairs with the targeting DNA strand of the protospacer DNA. Four guide sequences ranging from 20-nts to 26-nts used in a study described herein are listed. FIG. 1A discloses SEQ ID NOS 50-55, respectively, in order of appearance. FIG. 1B (Top) shows the domain organization for AceCas9. Conserved catalytic residues are indicated in red. RuvC refers to the RuvC nuclease domain (dark green), ABH refers to the Arginine-rich Bridge Helix (light green), REC refers to the heteroduplex Recognition lobe (grey), HNH refers to the HNH nuclease domain (dark blue), PID refers to the PAM-interacting domains and is composed of 3 segments: β-hairpin (β-H, orange), Topo-homology domain (TOPO, blue), and the C-terminal domain (CTD, light blue). FIG. 1B (Bottom left) shows SDS-PAGE analysis of the wild-type (WT) and H591A mutant AceCas9 following Nickel affinity chromatography (Ni-NTA), ion-exchange (IEC) and size-exclusion chromatography (S200). FIG. 1B (Bottom right) shows binding of AceCas9:sgRNA or H591A:sgRNA complex to single stranded targeting DNA labeled by HEX. Black line indicates the merged lanes from two different gels.

FIG. 2A shows cleavage results of double stranded DNA oligos (dsDNA) containing the 5'-NNNCC-3' PAM. FIG. 2A (Left) shows examination of HEX-labeled targeting DNA strand and its annealed dsDNA product in a non-denaturing gel. FIG. 2A (Right) shows cleavage of dsDNA labeled with fluorophore 6-FAM on its non-targeting strand (red) and cleavage of dsDNA labeled with fluorophore HEX on its targeting strand (green). FIG. 2B shows cleavage results of dsDNA oligos containing variations in PAM. FIG. 2B (Top) shows sequences and names of the wild-type and mutant oligo DNA. Mutations are indicated in red. FIG. 2B (Bottom) shows results of oligo DNA cleavage visualized on a 15% denaturing polyacrylamide gel. The two wild-type (WT) dsDNA are distinguished by the position of the fluorescence labels. The dsDNA with non-targeting strand labeled by 6-FAM is denoted as WT*, whereas that with targeting strand labeled by HEX is denoted as WT. Other dsDNA variants are indicated by nucleotides in red. FIG. 2B discloses SEQ ID NOS 56-68, respectively, in order of appearance.

FIG. 3A (Top left) shows a schematic representation of the pUC19 plasmid substrate for AceCas9 with protospacer and the PAM regions colored orange and blue, respectively. Names of the plasmids corresponding to the sequence variations (red) in the PAM region are shown to the right. FIG. 3A (Top right) shows sequences and names of a series of PAM mutations. Sequence alterations are colored red. (Bottom) Cleavage results by AceCas9:sgRNA at 37° C. and 50° C. for the wild-type and various mutant plasmids visualized by 0.5% agarose gel. FIG. 3A discloses SEQ ID NOS 69-75, respectively, in order of appearance. FIG. 3B shows the predicted site of cleavage (red arrows) by AceCas9 by sequencing the cleavage product on both strands of the wild-type plasmid. The sequences for the protospacer (yellow) and for the PAM (blue) are typed below the sequence traces. Asterisk denotes extra adenosine resulted from DNA sequencing. Related to FIGS. 7A-7B. FIG. 3B discloses SEQ ID NO: 76.

FIG. 4A shows a comparison of kinetic rate constants between a ssDNA substrate ($k_{cleave} \pm SD=0.65 \pm 0.10$ min$^{-1}$) and a dsDNA substrate ($k_{cleave} \pm SD=0.104 \pm 0.003$ min$^{-1}$). FIG. 4B shows a comparison of kinetic rate constants for the dsDNA containing one nucleotide bulge with PAM ($k_{cleave} \pm SD=0.179 \pm 0.007$ min$^{-1}$) and without the PAM ($k_{cleave} \pm SD=0.098 \pm 0.009$ min$^{-1}$). FIG. 4C shows a comparison of rate constants for BamHI-linearized plasmid DNA ($k_{cleave} \pm SD=0.10 \pm 0.01$ min$^{-1}$), supercoiled plasmid DNA ($k_{cleave} \pm SD=0.26 \pm 0.02$ min$^{-1}$), and gyrase-treated supercoiled DNA ($k_{cleave} \pm SD=0.30 \pm 0.02$ min$^{-1}$). FIG. 4D shows a comparison of rate constants for supercoiled plasmid DNA when using sgRNA with 20-nt spacer ($k_{cleave} \pm SD=0.26 \pm 0.02$ min$^{-1}$) and that with 24-nt spacer ($k_{cleave} \pm SD=1.04 \pm 0.03$ min$^{-1}$).

FIGS. 5A-5C. Plasmid Protospacer Specificity of Ace-Cas9. Plasmid substrates were incubated with molar excess AceCas9:sgRNA for one hour and the cleavage products were separated and visualized on a 1.0% agarose gel. Fraction of cleavage was calculated based on integrated band intensities. FIG. 5A shows sequences and names of a series of protospacer mutants in the pUC19 substrate for AceCas9:sgRNA. Mutated base pairs are shown in bold letters. FIG. 5A discloses SEQ ID NOS 77-82, respectively, in order of appearance. FIG. 5B shows a comparison of DNA cleavage by AceCas9:sgRNA between the wild-type and mutants for the supercoiled and BamHI-prelinearized plasmids and for reaction temperatures of 50° C. (FIG. 5B (Top)) and 37° C. (FIG. 5B (Botttom)). FIG. 5C shows quantified cleavage activities from reactions, the fraction of cleavage for the wild-type plasmid was normalized to 100%. FIG. 5C (Top) shows quantified cleavage activities for linearized for reaction temperature of 50° C. FIG. 5C (Second from Top) shows quantified cleavage activities for supercoiled for reaction temperature of 50° C. FIG. 5C (Second from Bottom) shows quantified cleavage activities for linearized for reaction temperature of 37° C. FIG. 5C (Bottom) shows quantified cleavage activities for supercoiled for reaction temperature of 37° C.

FIG. 6A shows a bacterial-based positive-selection assay was used to determine the activity of AceCas9 with sgRNA that contains either the 20-nt (FIG. 6A top row) or the 24-nt (FIG. 6A bottom row) spacer with 1:1000 cell dilutions. The AceCas9: sgRNA plasmids were transformed into competent cells with the ccdB plasmid that has a unique protospacer sequence and either a functional PAM (PAM$^{WT}$, 5'-NNNCC-3') or a double mutant of PAM (PAM$^{C(4,5)T}$, 5'-NNNTT-3'). Cells were selected in presence of antibiotics chloramphenicol (C$^+$) for AceCas9:sgRNA co-expression plasmid, or with both chloramphenicol and arabinose (C$^+$, Arabinose) to induce the expression of toxic ccdB gene. The right most plate illustrates low survival cells without dilution for the 20-nt spacer targeting wild-type plasmid, 24-nt spacer targeting PAM$^{C(4,5)T}$, or SpyCas9 targeting a non-cognate protospacer (ΔPS). FIG. 6B shows the cell survival assay of AceCas9 with 24-nt spacer sgRNA in comparison with SpyCas9 targeting the same plasmid. FIG. 6C shows percent of Escherichia coli survival in presence of arabinose were determined for SpyCas9 with a 20-nt spacer (96%±25%), AceCas9 with a 20-nt spacer (<0.01%), AceCas9 with a 22-nt spacer (<0.01%), AceCas9 with a 24-nt spacer (75%±6%), and AceCas9 with 26-nt spacer (13.6%±0.4%) sgRNA that target the ccdB plasmid with PAM$^{WT}$. Percent survival were also determined for AceCas9 with 24-nt spacer (<0.001%) and 26-nt spacer (<0.001%) sgRNA target the ccdB plasmid with PAM$^{C(4,5)T}$. Each experiment was performed in triplicate.

FIG. 7A shows experimental design of DNA library cleavage assay to determine PAM sequence for AceCas9. FIG. 7B shows a smaller cleavage product (~500-bp) that contains PAM sequences was released after the double digestion cleavage with AceCas9 and BamHI. Color-inverted, contrast-adjusted image (left) shows the ~500-bp cleavage product from the original gel image (right). FIG. 7C shows DNA sequences of 18 clones were aligned using Clustal Omega (Sievers et al., 2011). (Right) PAM sequence regions were extracted and aligned using WebLogo (Crooks et al., 2004). FIG. 7C discloses SEQ ID NOS 83-100, respectively, in order of appearance.

FIG. 8A shows various oligo DNA substrates (with HEX-labeled on targeting DNA strand) were subjected to cleavage assay by AceCas9 and HNH-inactivated AceCas9 (H591A). H591A AceCas9 does not cleave neither ssDNA (WT*) nor the targeting strand of dsDNA (WT). The result using substrate PAM-C4,5G‡ (red box) was used in FIG. 2B. FIG. 8B shows a wild-type (WT2) and targeting strand-mutated dsDNA (PAM-G4,5C*), with 6-FAM labeled on non-targeting DNA strand, were subjected to cleavage assay by wild-type AceCas9 (AceCas9 WT) and HNH-inactivated AceCas9 (AceCas9 H591A). AceCas9 H591A cleaves the non-targeting DNA strand of WT2, suggesting that the RuvC domain of AceCas9 H591A remains active. The result of AceCas9 WT treated with substrate PAM-G4,5C* (red box) was used in FIG. 2B. FIG. 8B (Bottom) discloses SEQ ID NOS 101-103, respectively, in order of appearance.

FIG. 9B shows AceCas9 linearized plasmid DNA in a broad range of temperature (25-60° C.). Reactions were performed identical to regular plasmid cleavage assay, with reaction tubes incubated at a temperature-equilibrated water bath for 60 minutes. Black line indicates the boarder of two separate gels.

FIG. 10C shows pUC19 plasmids (supercoiled plasmid) treated with either BamHI (linearized plasmid) or E. coli gyrase (gyrase-treated plasmid) were resolved by 1% 1×TBE (with 10 µg/mL chloroquine, Sigma-Aldrich) agarose gel in 1× chloroquine-added TBE running buffer in 2.5 V/cm for 14 hours. Gel was rinsed in ddH$_2$O for 2 hours followed by incubation in SYBR Gold (Thermo Fisher Scientific) for 30 minutes. The gel was visualized by Chemi-Doc XRS System (Bio-Rad). Chloroquine was added to help visualize supercoiling of the plasmid DNA substrates (Shure et al., 1977).

DETAILED DESCRIPTION

Figure 1A:
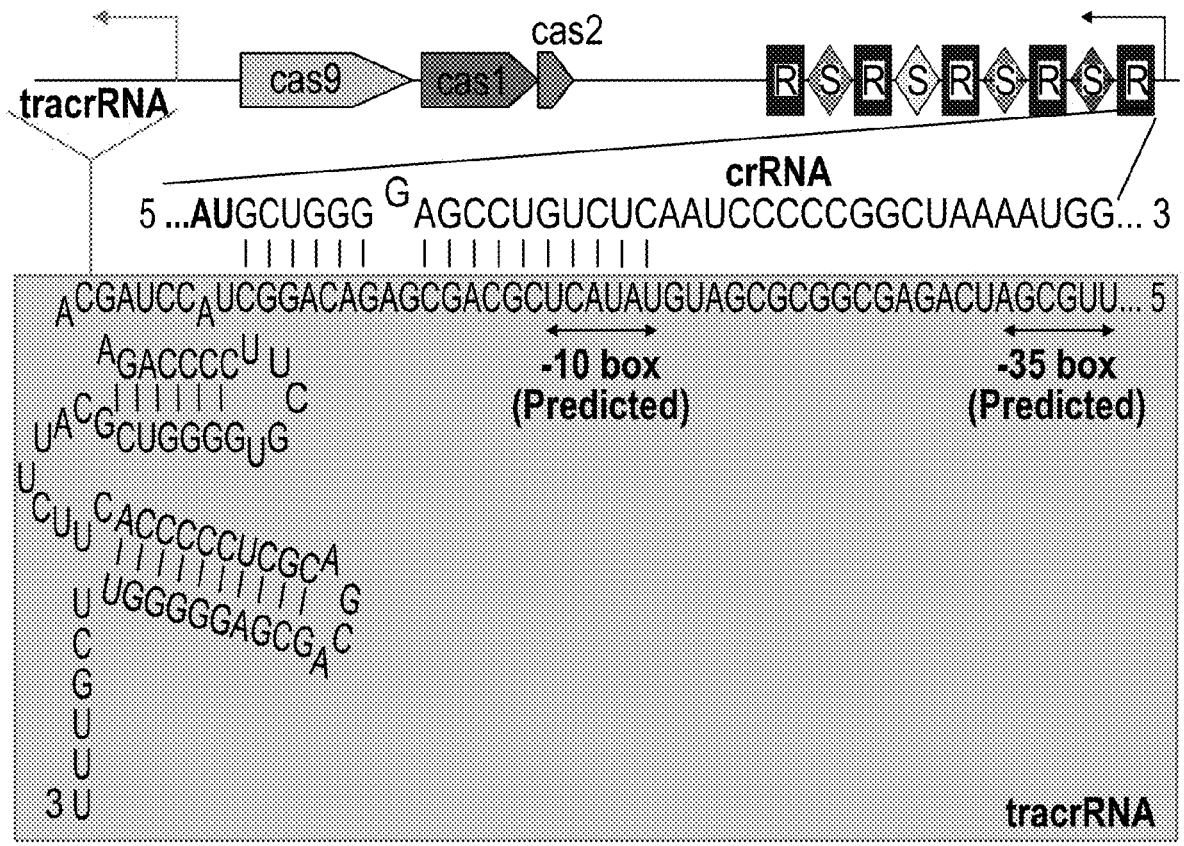
FIGS. 1A-1B. Identification and Purification of the Type II-C Cas9 from *A.cellulolyticus* (AceCas9).
Figure 1A:
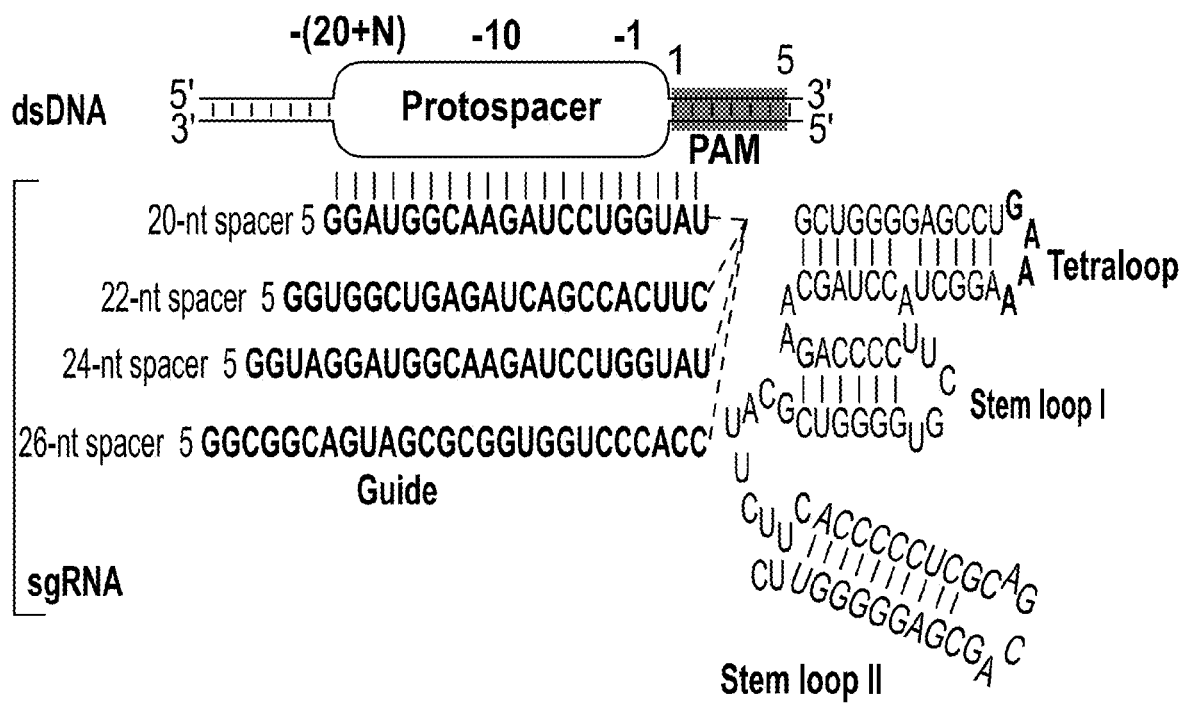

Provided herein are methods and compositions for rapid and precise genome editing at any desired genomic position in almost all cells and organisms. The methods utilize a cytosine-specific Cas9 endonuclease and are suitable for applications requiring targeting cytosine adjacent DNA. The methods generally include introducing a cytosine-specific Cas9 endonuclease, a single guide RNA, and optionally a desired nucleic acid repair template that is utilized in either non-homologous end joining or homology directed repair. The methods can be used to effect gene knockout, gene knockdown, gene substitution, or gene introduction in cells and organisms.

Methods for specifically manipulating nucleic acids in a cell or organism are provided. The methods can include contacting the cell or organism with a cytosine-specific Cas9 endonuclease and a single guide RNA (sgRNA) targeting a protospacer sequence of the nucleic acids that is adjacent to a Protospacer Adjacent Motif (PAM) sequence of the nucleic acids. The methods can also include contacting the cell or organism with a desired nucleic acid repair template (e.g. a DNA template). The cytosine-specific Cas9 endonuclease can be a Type II-C Acidothermus cellulolyticus Cas9 (Ace-Cas9). The PAM sequence can be downstream of the protospacer sequence on a non-targeting strand of the nucleic acids. The PAM sequence can be five, six, seven, or eight nucleotides. The PAM sequence can be five nucleotides and selected from one of the following sequences: 5'-NNNCN-3', 5'-NNNNC-3', or 5'-NNNCC-3'. The PAM sequence can have a cytosine at position 4, position 5, or both positions 4 and 5. The sgRNA can comprise an 18, 19, 20, 21, 22, 23, 24, 25, or 26 nucleotide guide region complementary to the protospacer sequence, or any ranges thereof (e.g. 18-26, 24-26). The ambient temperature of the cell or organism (e.g. external temperature surrounding the cell or organism) can be 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60° C., or any ranges thereof (e.g. 25-60° C., 36-38° C., 50-60° C.). The nucleic acids to be manipulated can be deoxyribonucleic acids (DNA). The nucleic acids to be manipulated can be supercoiled. The nucleic acids to be manipulated can be linearized. The nucleic acids to be manipulated can be a plasmid or a portion thereof. The nucleic acids to be manipulated can be a chromosome or a portion thereof. The cell can be a bacterial cell, a fungal cell, an archaea cell, a plant cell, or an animal cell. The organism can be a bacteria, a fungus, an archaea, a plant, or an animal. The cell or organism may not have a native cytosine-specific Cas9 endonuclease, a native single guide RNA, and/or a native desired nucleic acid repair template (e.g. the cell or organism as it exists is nature does not have a cytosine-specific Cas9 endonuclease, a single guide RNA, and/or a desired nucleic acid repair template absent human intervention). The cell or organism can be contacted with the cytosine-specific Cas9 endonuclease, the sgRNA, and optionally the desired nucleic acid repair template for at least 10, 20, 30, 40, 50, 60, 90, 120, or more minutes. Contacting the cell or organism with the cytosine-specific Cas9 endonuclease, the sgRNA, and optionally the desired nucleic acid repair template can introduce at least one nucleotide insertion, deletion, and/or substitution in the nucleic acids. Contacting the cell or organism with the cytosine-specific Cas9 endonuclease, the sgRNA, and optionally the desired nucleic acid repair template can cause: (i) disruption of a protein-encoding gene of the nucleic acids (e.g. by knockout or knockdown), (ii) replacement of the protein-encoding gene of the nucleic acids with a substitute gene (e.g. based on the desired nucleic acid repair template), or (iii) introduction of a new gene into the nucleic acids (e.g. based on the desired nucleic acid repair template).

In embodiments, a single guide RNA can be a polyribonucleic acid sequence that can form a complex with a cytosine-specific Cas9 endonuclease and enables the cytosine-specific Cas9 endonuclease to recognize and cleave a target site on a polynucleotide such as DNA. A single guide RNA can comprise a first nucleotide sequence domain that is complementary to a nucleotide sequence in a target DNA (e.g. a variable targeting domain) and a second nucleotide domain that interacts with a cytosine-specific Cas9 endonuclease polypeptide (e.g. an endonuclease recognition domain). In general, a single guide RNA has sufficient complementarity with a target polynucleotide sequence to hybridize with the target sequence and direct sequence-specific binding of a CRISPR complex to the target sequence. In embodiments, the degree of complementarity between a single guide RNA and its corresponding target sequence, when optimally aligned using a suitable alignment algorithm, is about or at least about 80%, 85%, 90%, 95%, 96%, 97%, 98%, 99%, 99.5%, 99.9%, or 100%. A single guide RNA may be selected to target any target sequence. In embodiments, the target sequence is a sequence within a genome of a cell. Exemplary target sequences include those that are unique in the target genome.

In embodiments, a cytosine-specific Cas9 endonuclease may recognize a protospacer adjacent motif (PAM) sequence comprising one of the following sequences: 5'-NNNCN-3', 5'-NNNNC-3', or 5'-NNNCC-3'. In embodiments, a cytosine-specific Cas9 endonuclease can direct cleavage of one or both strands of a target DNA at the location of a target sequence, such as within the target sequence and/or within the complement of the target sequence. In embodiments, a cytosine-specific Cas9 endonuclease directs cleavage of one or both strands of a target DNA within about, or at least about, 1, 2, 3, 4, 5, 6, 7, 8, 9, 10, 15, 20, 25, or 50, or more base pairs from the first or last nucleotide of a target sequence.

In embodiments, DNA cuts generated by a cytosine-specific Cas9 endonuclease may be corrected using different cellular repair mechanisms, including error-prone Non-homologous End Joining (NHEJ) and high-fidelity Homology Directed Repair (HDR) using a desired nucleic acid repair template (e.g. DNA template). A desired nucleic acid repair template is typically integrated into a genome using homology directed repair.

In embodiments, methods of the disclosure can selectively add, delete, replace, or mutate genes or segments of a genome. In embodiments, methods of the disclosure can target any locus in a genome. In embodiments, methods of the disclosure can be used to treat or combat pathogens, viruses, bacteria, pathogens, insects, diseases, or conditions by gene therapy. In embodiments, methods of the disclosure can be used to generate specific strains, breeds, or mutants of a model organism. In embodiments, methods of the disclosure can be used to selectively add, delete, or mutate nucleic acids in viruses, prokaryotes, eukaryotes, protists, fungi, plants, invertebrate animals, or vertebrate animals, In embodiments, methods of the disclosure can be used to selectively add, delete or mutate nucleic acids in a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, or a rabbit. In embodiments, the methods of the disclosure can be used to create new organisms with de novo characteristics. In embodiments, the methods of the disclosure can be used to integrate nucleic acids of any suitable size into a genome (e.g. integration of a desired nucleic acid repair template by homology directed repair).

In embodiments, a cytosine-specific Cas9 endonuclease, a single guide RNA, and optionally a desired nucleic acid repair template may be introduced into a host cell or organism using methods well-known to those of ordinary skill in the art. In embodiments, cells or organisms may be genetically engineered by transfection or transduction with a vector or a plasmid (e.g., an expression construct) expressing the elements described herein, such as a cytosine-specific Cas9 endonuclease and a single guide RNA. In embodiments, a nucleic acid may be introduced into a host cell or organism by, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, direct micro injection, nanoparticle-mediated nucleic acid delivery, and the like.

EXAMPLES

Cas9 is a RNA-guided DNA cleavage enzyme being actively developed for genome editing and gene regulation. Cas9 cleaves double stranded DNA containing a protospacer sequence that is complementary to the guide region of a Cas9-bound guide RNA (typically 20-nucleotides in length) and adjacent to a short Cas9-specific element called Protospacer Adjacent Motif (PAM). Understanding the correct juxtaposition of the protospacer- and PAM-interaction with Cas9 enables development of versatile and safe Cas9-based technology.

The present disclosure identifies Cas9s that recognize different PAM sequences than are currently known and that possess desired biochemical properties for high specificity. This disclosure provides identification and biochemical characterization of a Cas9 from *Acidothermus cellulolyticus* (AceCas9) (type II-C) that, unlike previously characterized Cas9s, recognizes a 5'-NNNCC-3' PAM.

Kinetic studies indicate that AceCas9 has a preference for negatively supercoiled DNA and is significantly more specific for relaxed than for supercoiled protospacers. Rephrased, AceCas9 is more efficient in cleaving negative supercoils than relaxed DNA. Kinetic studies as well as in vitro and in vivo activity assays also showed that AceCas9 achieves optimal activity when combined with a sgRNA containing a 24-nucleotide complementarity region. The cytosine-specific, DNA topology-sensitive, and extended guide-dependent properties of AceCas9 are suitable for specific genome editing applications.

Results

Purification and Characterization of AceCas9 Ribonucleoprotein Particle

Figure 1B:
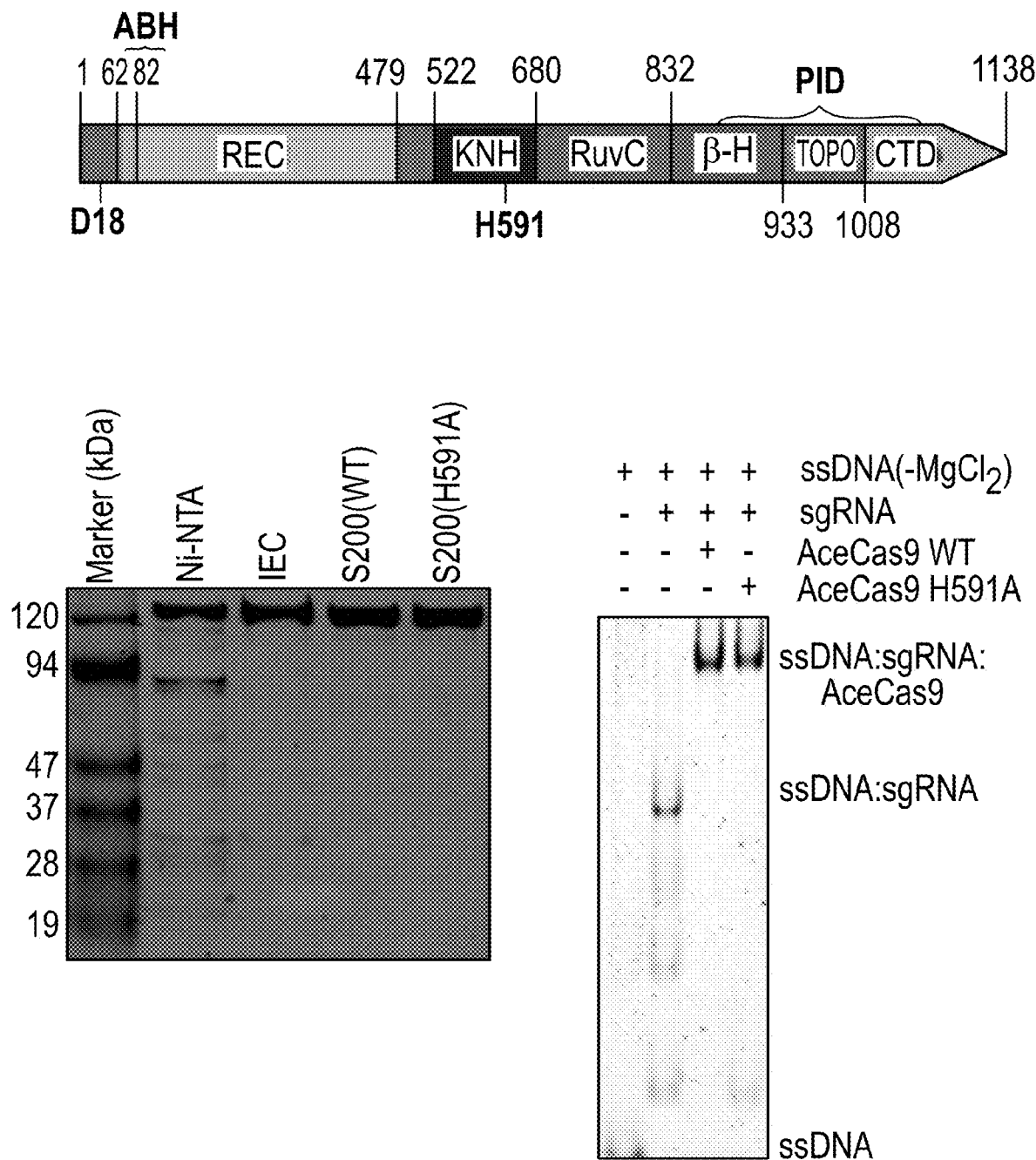

Following early bioinformatics methods in identifying Cas9 orthologs, Cas9 from a thermophile, A.cellulolyticus 11B (optimal growth temperature 55° C.), was identified. Recombinant AceCas9 was expressed and purified to homogeneity by using three chromatography steps (FIG. 1B). To identify its associated tracrRNA, the available A. cellulolyticus consensus direct repeat sequence on CRISPRdb was used to identify a match to sixteen bases (with one mismatch) in the noncoding region downstream of the cas9 gene following putative transcription start sites (FIG. 1A). The resulting tracrRNA was 83-nt in length and predicted by mfold to contain two stem loops (a 6-bp stem loop I and a 10-bp stem loop II) (FIG. 1A). Based on previous Cas9 studies that sgRNA is fully functional, a sgRNA was generated by linking the tracrRNA and crRNA through a 5'-GAAA-3' tetraloop (FIG. 1A). The AceCas9:sgRNA ribonucleoprotein particle (RNP) was able to shift and cleave a Hexachloro-fluorescein phosphoramidite (HEX)- or 6-carboxyfluorescein (6-FAM)-labeled DNA oligo complementary to the 20-nt spacer (FIG. 1B).

AceCas9 has a Double Cytosine PAM

Figure 7A:
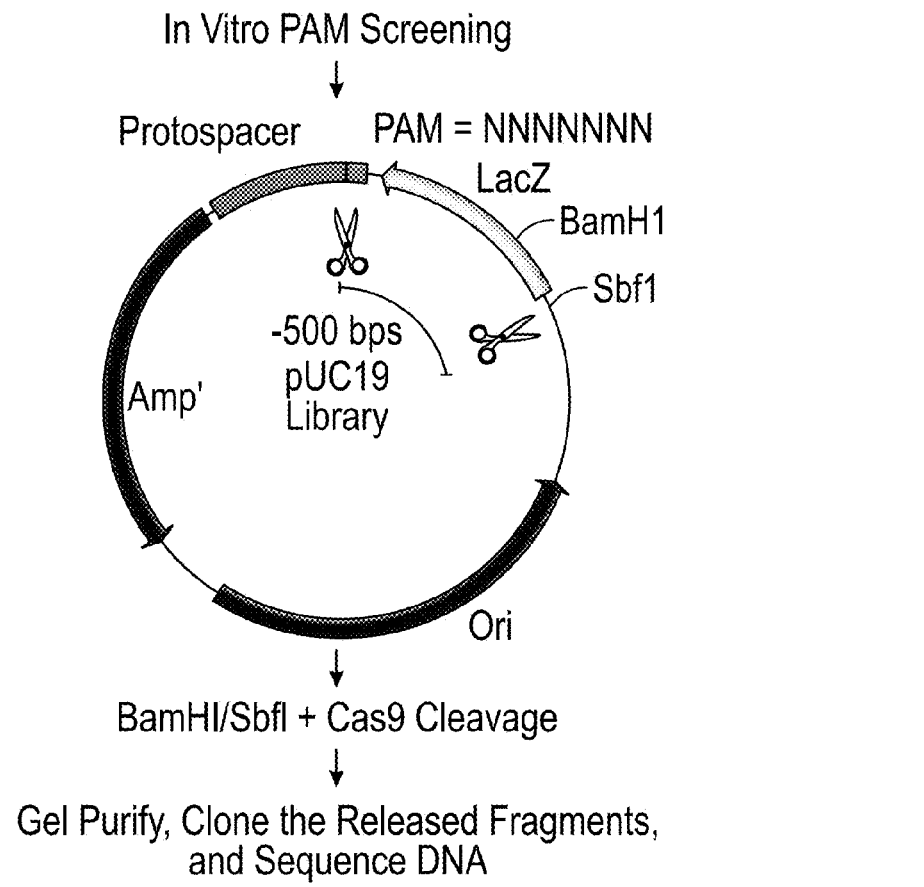
FIGS. 7A-7C. In vitro PAM determination by DNA Library Cleavage Assay. Related to FIGS. 2A-2B and 3A-3B.
Figure 7B:
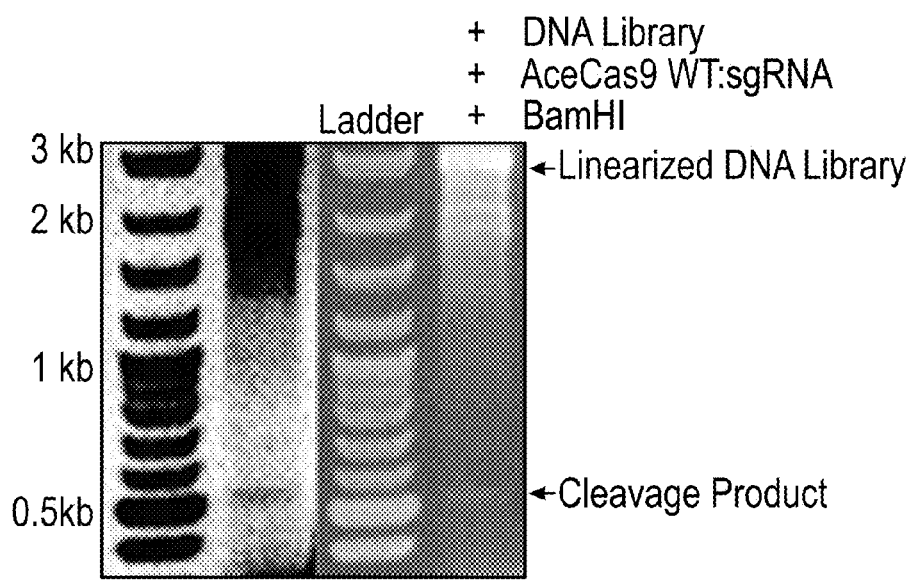
Figure 7C:
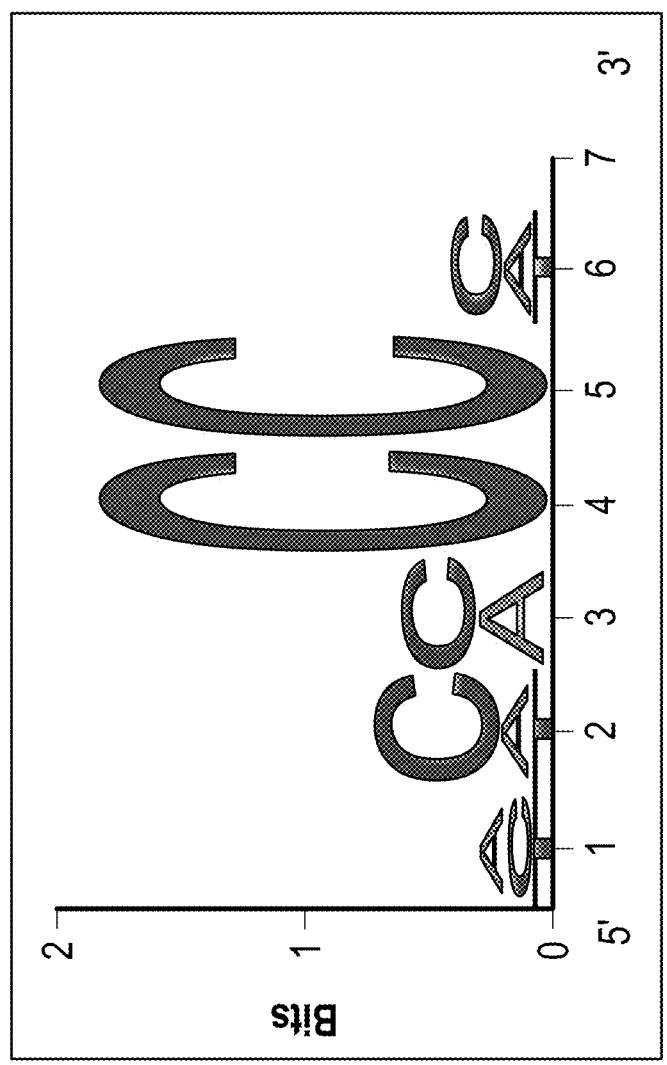

Sequence search did not yield matches in various databases using Nucleotide BLAST and CRISPRTarget to any of the 23 spacer sequences in A.cellulolyticus CRISPR locus. Therefore, the PAM sequences for AceCas9 could not be identified by comparing the flanking regions of the potential protospacers. A DNA library bearing random sequences in the PAM region was designed and constructed as the substrates for AceCas9 cleavage (FIG. 7A). The PAM region contains seven randomized base pairs (5'-NNNNNNN-3' with a 25% probability for each base pair at any given position) and is located downstream of a 20-nt protospacer inserted into the pUC19 plasmid (FIG. 7A). The potential AceCas9 cleavage site is located ~500 base pairs from that of BamHI, which allowed the generation of DNA fragments from AceCas9:sgRNA/BamHI cleavage (FIG. 7B) for cloning and Sanger sequencing. Thirty-four ~500-bp fragments were successfully cloned and sequenced, among which 18 contained the PAM-protospacer insertion (FIG. 7C). Strikingly, the 18 clones that contained the insertion all had cytosine at positions 4 and 5 downstream of the protospacer on the non-targeting DNA strand, indicating that 5'-NNNCC-3' is a functional PAM for AceCas9 (FIG. 7C).

Figure 2A:
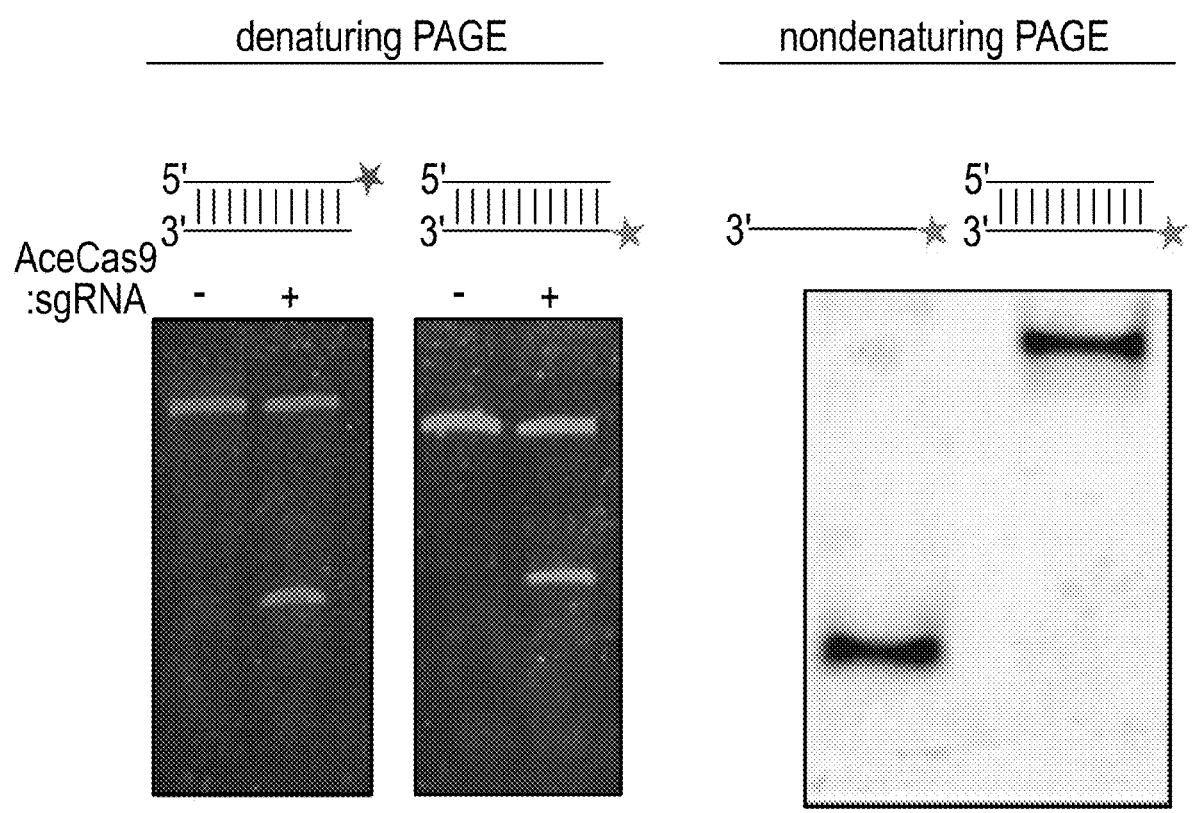
FIGS. 2A-2B. Experimental Confirmation of the 5'-NNNCC-3' PAM for AceCas9 on Oligo DNA Substrates.
Figure 2B:
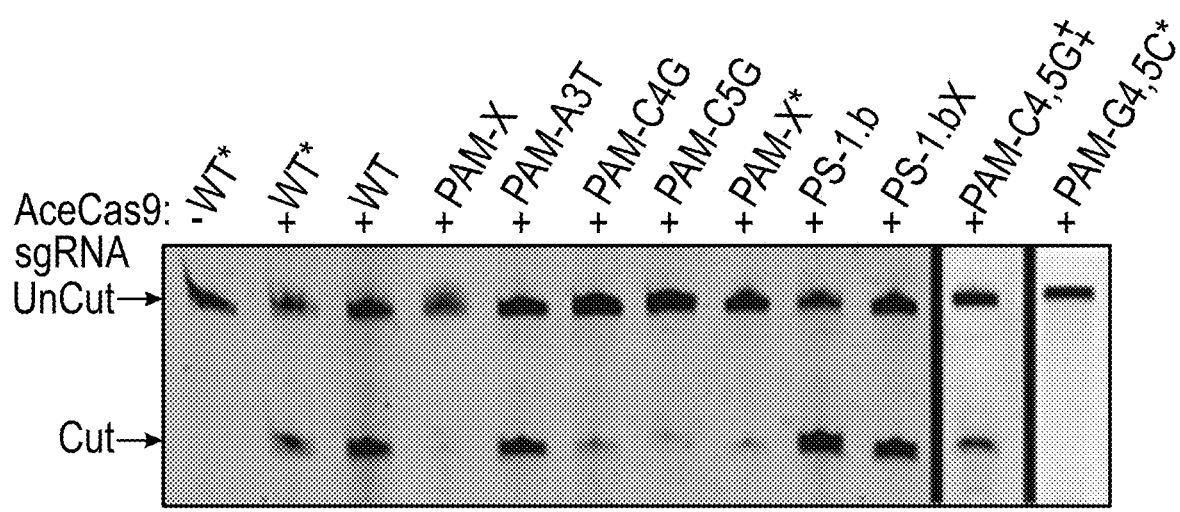
Figure 8A:
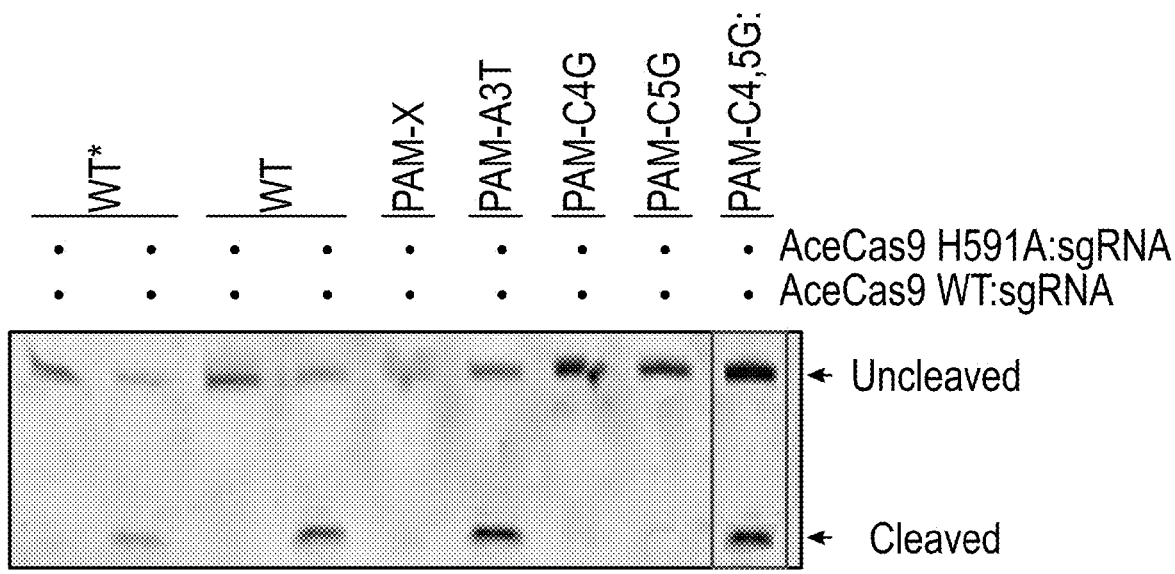
FIGS. 8A-8B. Oligo DNA Cleavage Activity of AceCas9 and AceCas9 mutants.
Figure 8B:
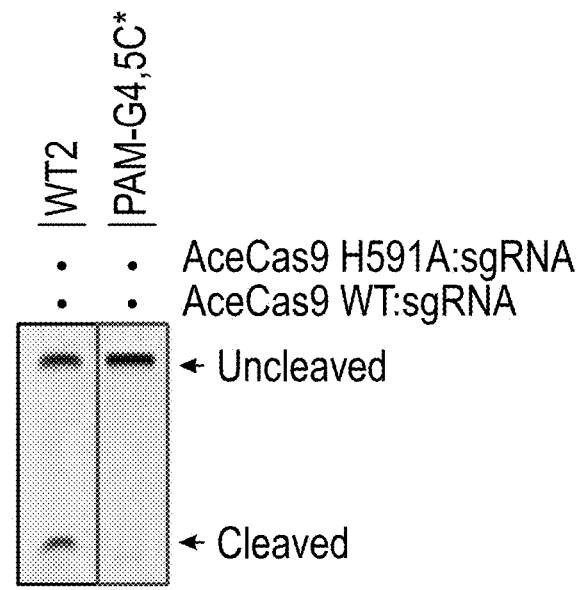

To observe the PAM-activated DNA cleavage activity of AceCas9, a series of dsDNA oligos containing the 5'-NNNCC-3' PAM and its variants were synthesized. The dsDNA was ether labeled with HEX on the targeting strand or with 6-FAM on the non-targeting strand (FIG. 2B and FIG. 8B). In a typical cleavage experiment, 1.2-20 molar excess of non-labeled DNA was used to ensure formation of the dsDNA substrate for AceCas9 (FIG. 2A). Wild-type AceCas9 cleaved dsDNA oligos efficiently only when the correct PAM was present (FIG. 2B, FIG. 8A, and FIG. 8B), while HNH-inactivated AceCas9 (H591A AceCas9) can only cleave the non-targeting DNA strand of the same oligo (FIGS. 8A and 8B). Compensatory mutations of nucleotide sequences at PAM positions 4 or 5 greatly reduced cleavage activity by AceCas9 (FIG. 2B and FIG. 8A). Intriguingly, the cleavage defect on these PAM mutants could be rescued if the protospacer contained a bulge at position −1 (FIG. 2B) or when the two guanine nucleotides base paired with dC4 and dC5 were unchanged (FIG. 2B and FIG. 8A). These results indicate a dependence of AceCas9 on the C-G base pair at positions 4 and 5 but, more importantly, the guanine bases paired with dC4 and dC5 in DNA cleavage.

Figure 3A:
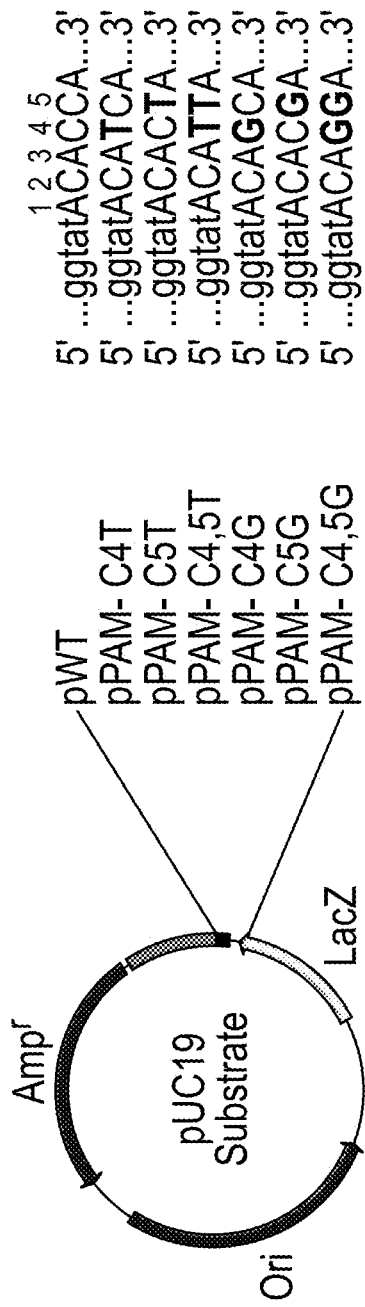
FIGS. 3A-3B. Experimental Confirmation of the 5'-NNNCC-3' PAM for AceCas9 on Plasmid DNA Substrates.
Figure 3A:
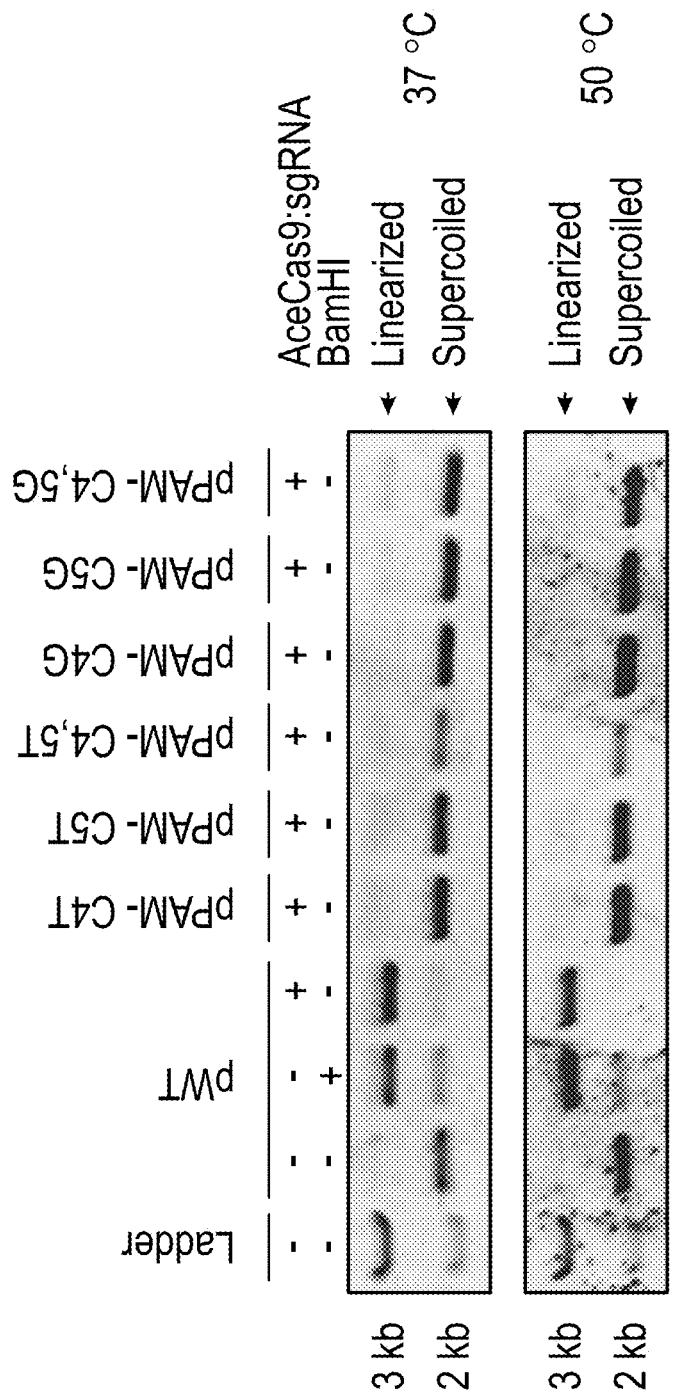
Figure 3B:
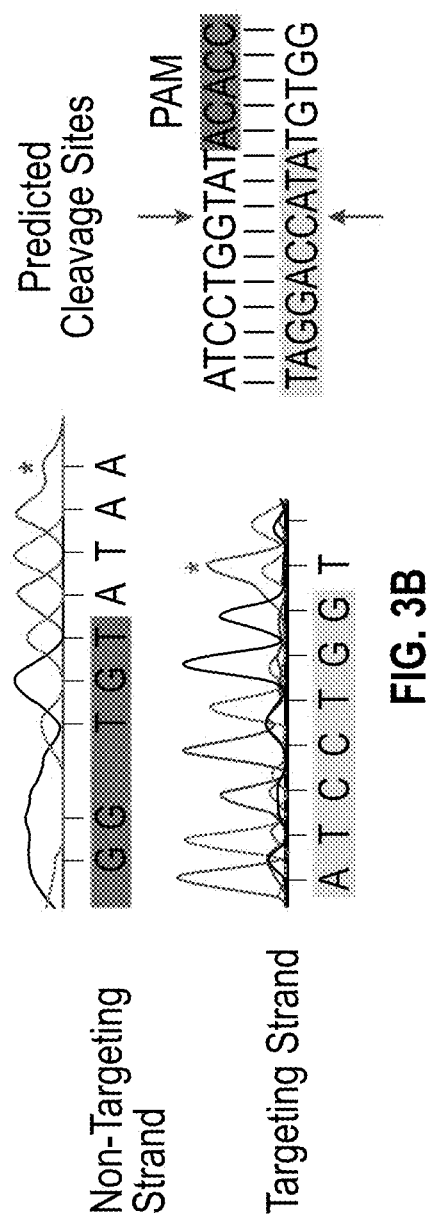
Figure 9A:
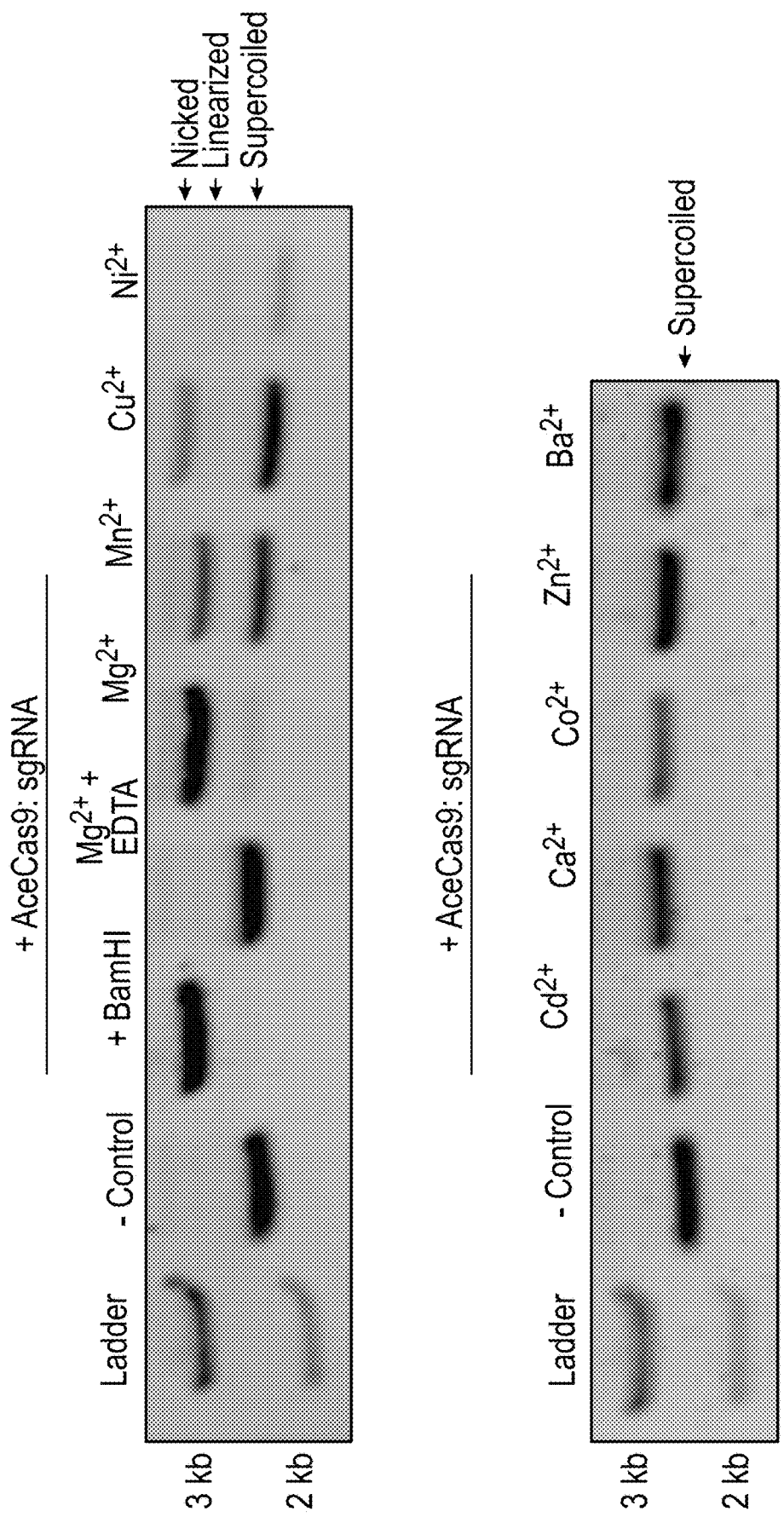
FIGS. 9A-9B. AceCas9 is Adaptable to Temperature Variation, but Selective to Metal Ions for Cleavage Activity. Related to FIGS. 3A-3B and 5A-5C, FIG. 9A (Top and Bottom) shows a plasmid cleavage assay was performed with various divalent cations or divalent metal chelator. AceCas9 cleaves dsDNA plasmid in presence of Mg$^{2+}$ and Mn$^{2+}$, while generating nicked DNA in presence of Cu$^{2+}$.
Figure 9B:
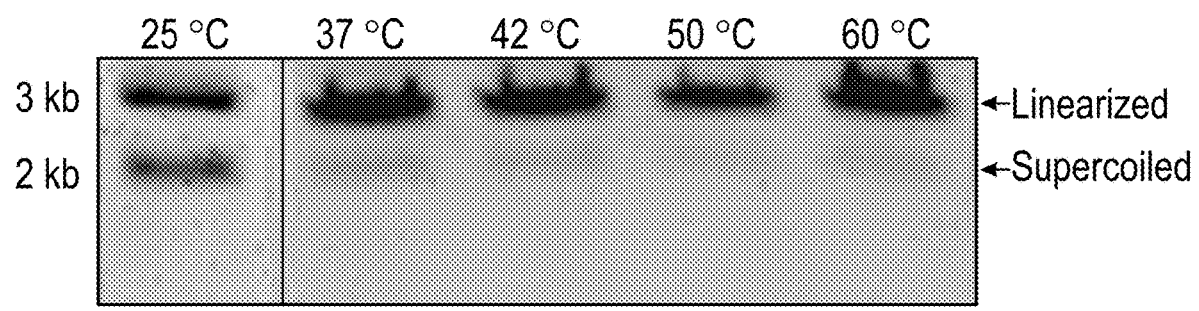
Figure 10A:
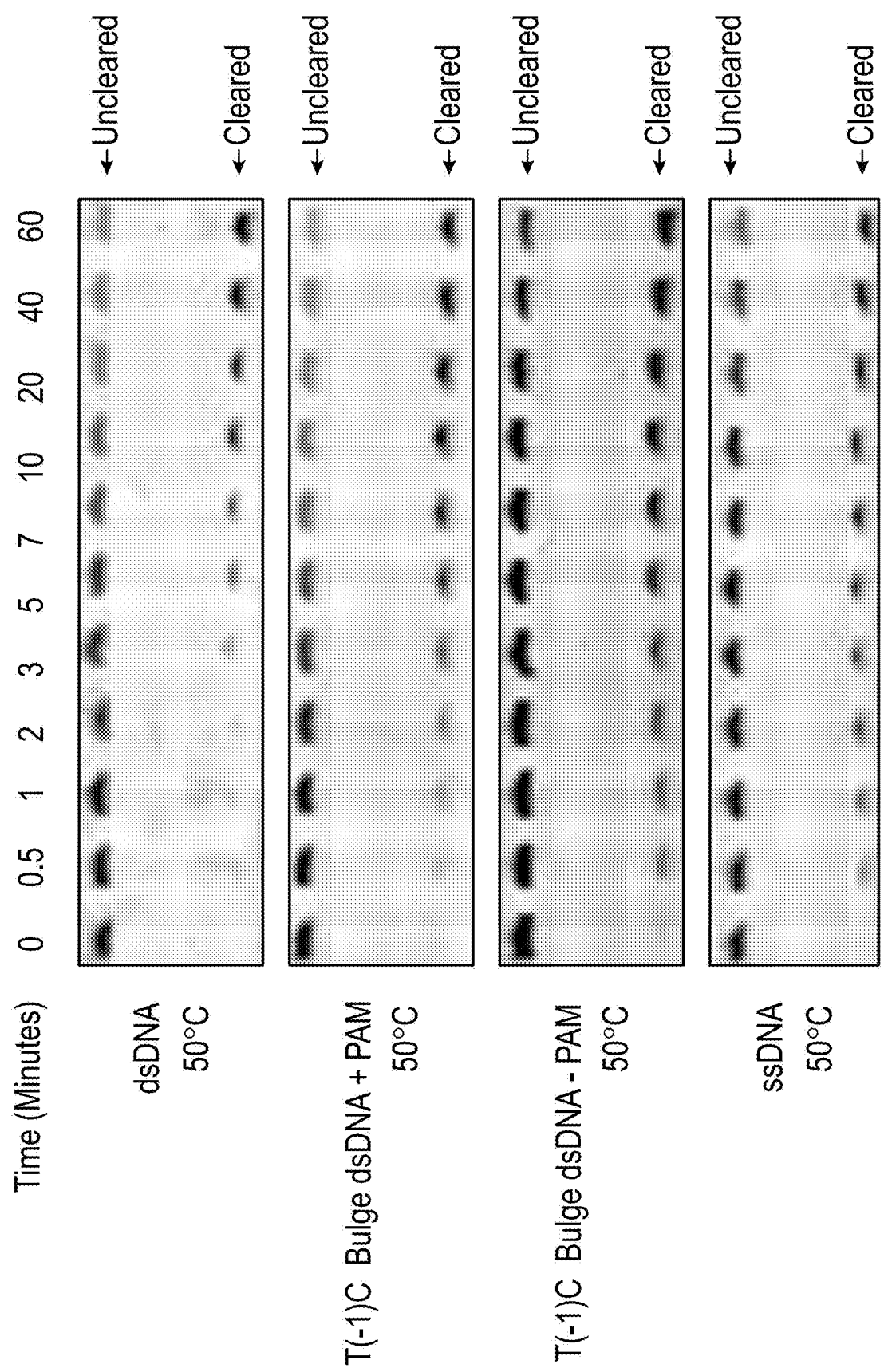
FIGS. 10A-10C. Single-turnover Kinetic Assays with Oligo and Plasmid DNA Substrates. Related to FIGS. 4A-4D, FIGS. 10A and 10B show representative gel images for each set of kinetics assays using (FIG. 10A) 30-nt oligonucleotide substrates or (FIG. 10B) 3-kb plasmid substrates. Pre-aliquoted samples were placed on ice and gel loading buffer (with EDTA) was added at the indicated time points to stop the reaction. Each experiment was performed in triplicate.
Figure 10B:
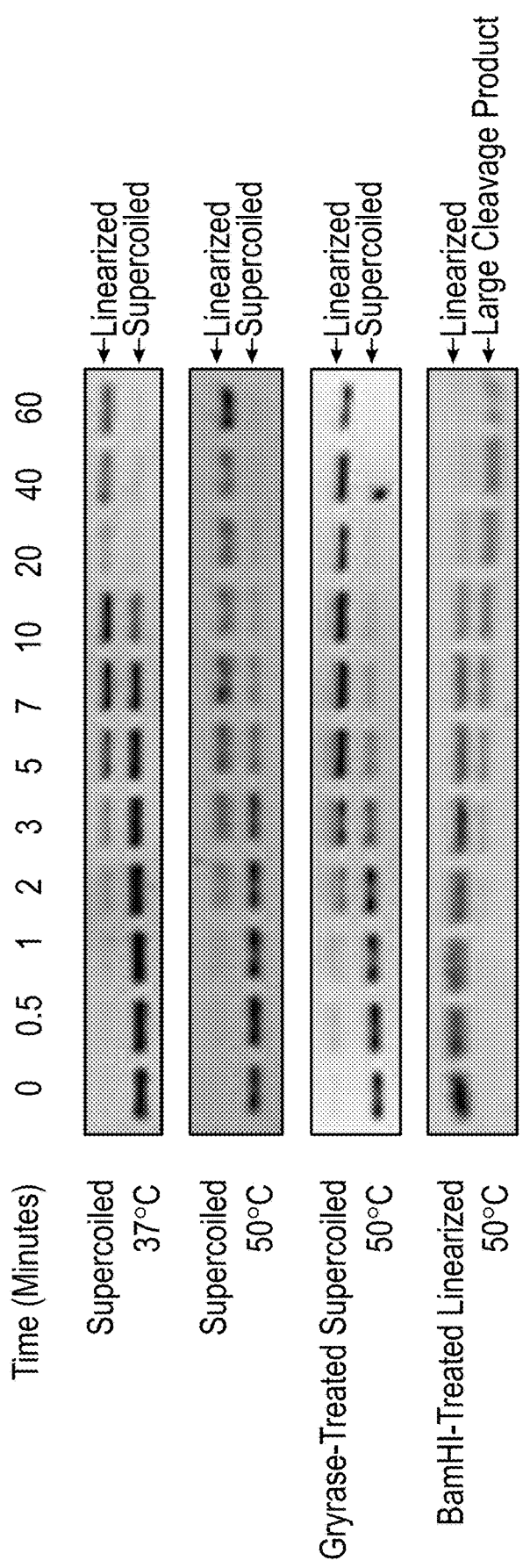
Figure 10C:
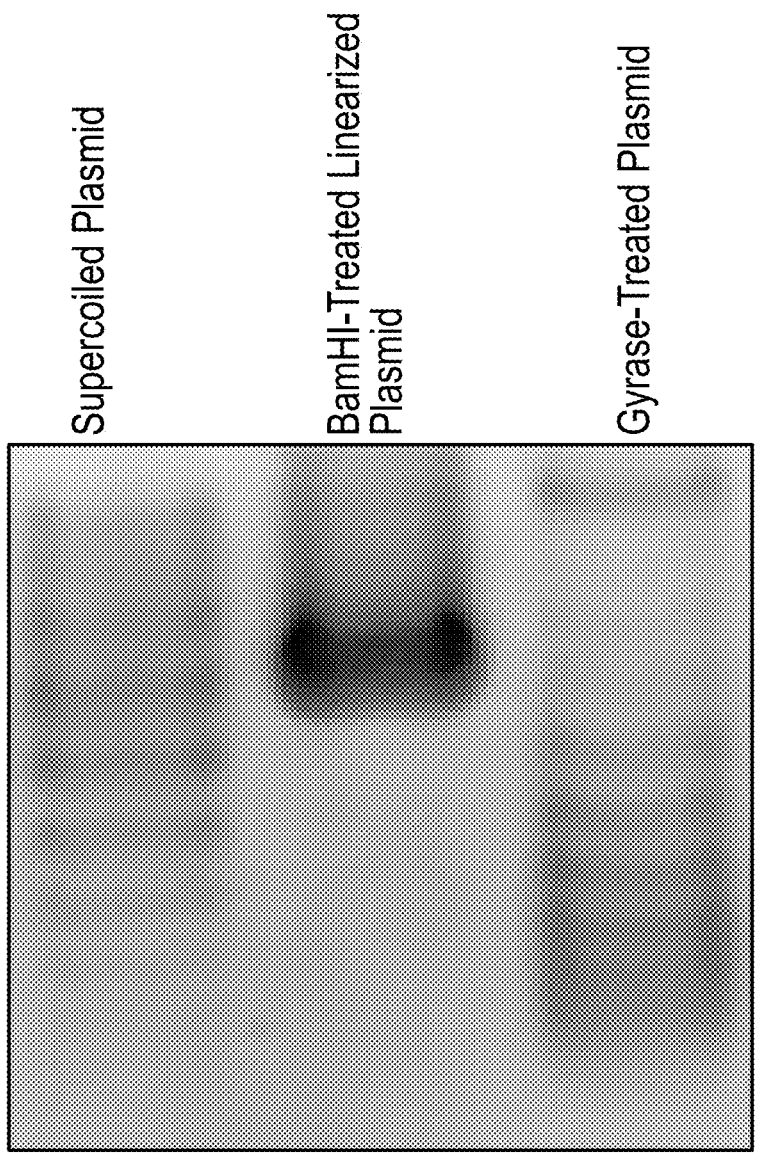

AceCas9 activity on plasmid substrates was subsequently tested. Consistently, AceCas9 also cleaved the plasmid substrate containing the 5'-NNNCC-3' PAM, and not those with dC4/5 to G or dC4/5 to T mutations (FIG. 3A). The cleavage sites on the plasmid were mapped by DNA sequencing to the phosphodiester bond between the third and the fourth nucleotides upstream of the PAM (FIG. 3B). The cleavage specifically required magnesium, but tolerated manganese and generated a nick with copper (FIG. 9A). Furthermore, due to its thermostability, AceCas9 is active at temperatures 25° C.-60° C. (FIG. 9B).

DNA Unwinding Limits AceCas9 Cleavage Efficiency

Figure 4A:
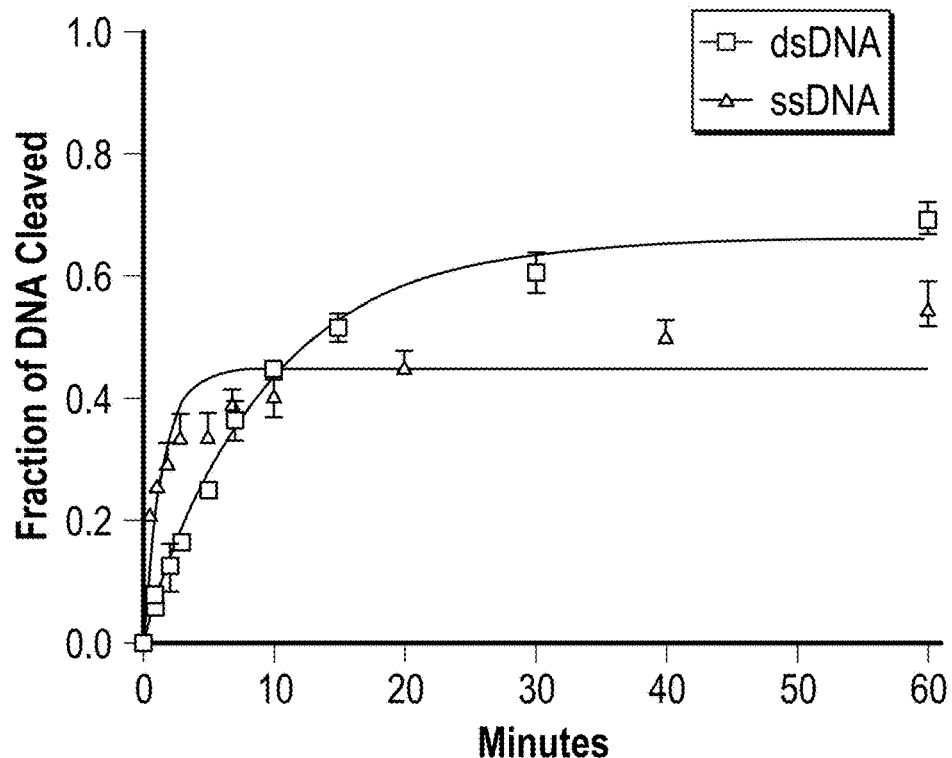
FIGS. 4A-4D. Kinetic Analysis of DNA Cleavage by AceCas9. Single turnover cleavage assays with AceCas9: sgRNA were performed at 50° C. in triplicate. The fraction of cleaved were quantified and fitted to a single exponential function to extract pseudo first-order rate constant, $k_{cleave}$, for each reaction. Related to FIGS. 10a-10b.
Figure 4B:
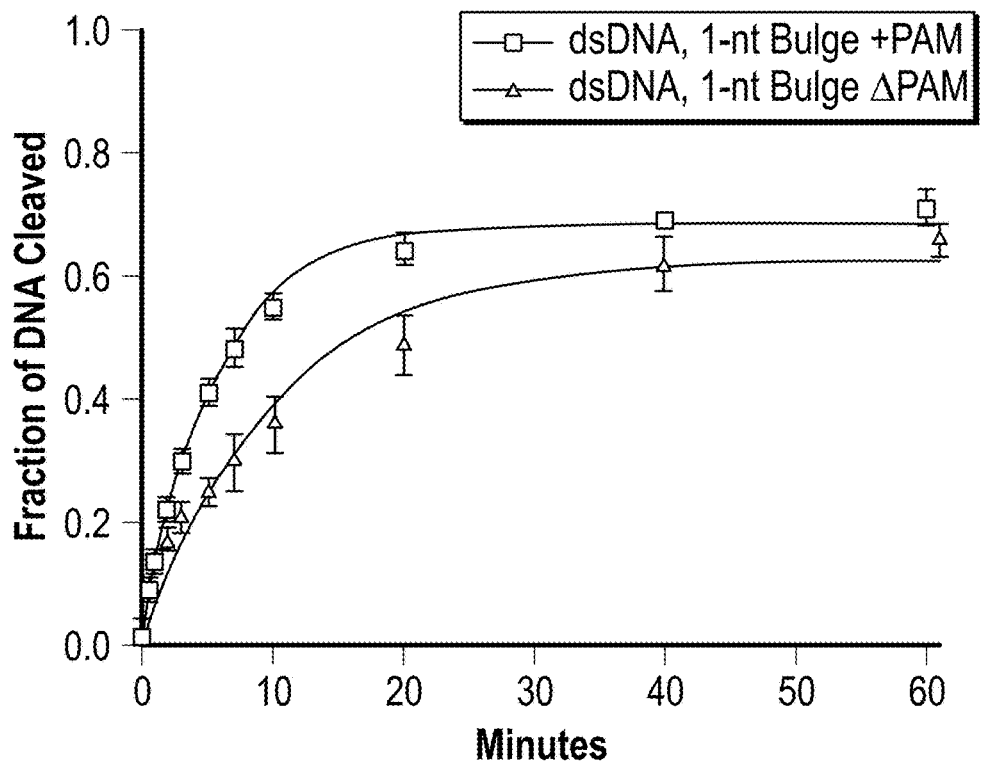
Figure 4C:
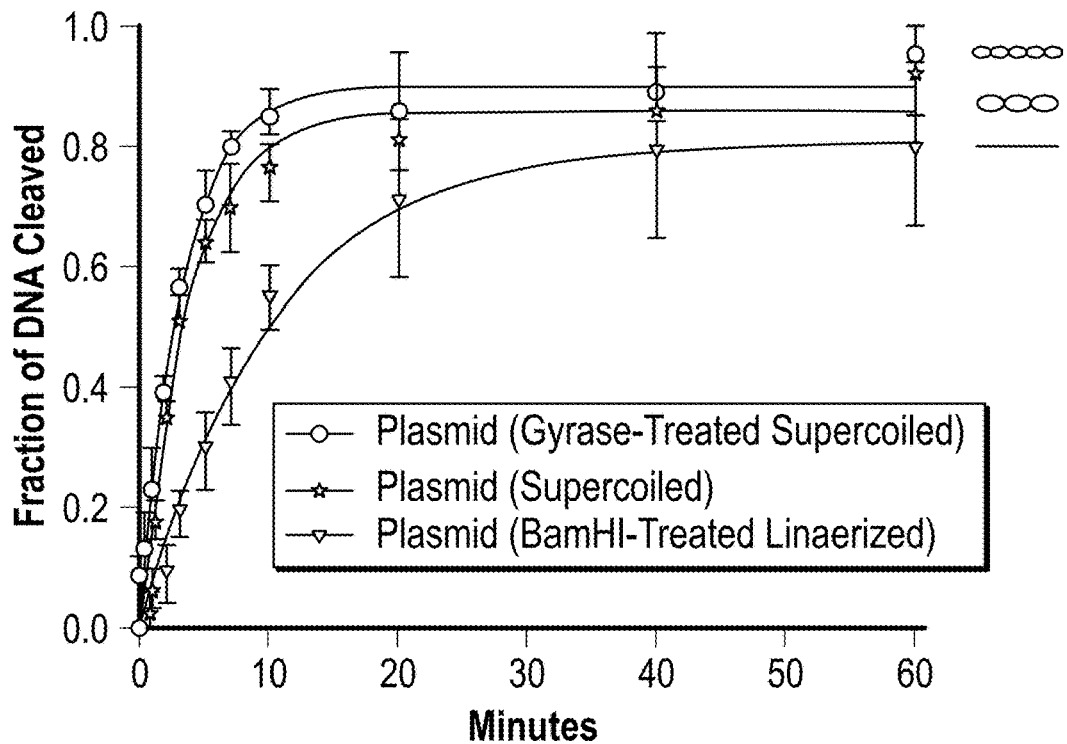

To understand the cleavage efficiency of AceCas9, both oligo and plasmid substrates were subjected to single-turnover kinetics analysis (FIGS. 4A-4D and Table 1). Under this condition, the measured cleavage rate depends on steps following AceCas9 binding to the substrates that may include unwinding the DNA, conformational change in the catalytic domains and the cleavage step itself. Although AceCas9 cleaved ssDNA the fastest ($k_{cleavage}$=0.65±0.10 min$^{-1}$), the fraction of cleavage plateaued at ~50% (FIG. 4A), indicating the possible presence of nonproductive substrates. Consistently, dsDNA oligo ($k_{cleavage}$=0.104±0.005 min$^{-1}$) was cleaved to ~70% (FIG. 4A) and the circular plasmid substrate ($k_{cleavage}$=0.26±0.02 min$^{-1}$) was cleaved to more than 90% (FIG. 4C). To understand which functional step in AceCas9 cleavage limits its cleavage efficiency, an experiment measured the rate constant for the dsDNA containing a bulge at −1 position (FIG. 4B) and found that its cleavage was nearly 1.7-fold ($k_{cleavage}$=0.179±0.007 min$^{-1}$) of the fully base-paired dsDNA, indicating that DNA unwinding is likely the rate-limiting step (FIG. 4A).

Figure 4D:
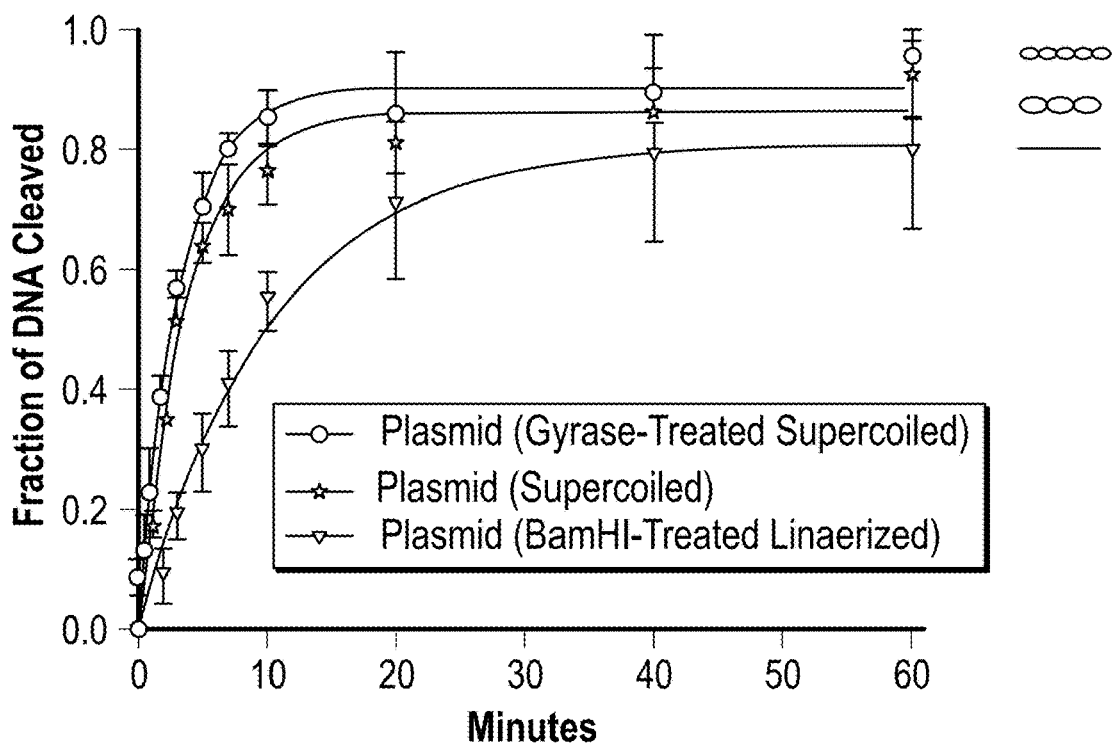

Another experiment then tested if enhanced complementarity between the spacer and protospacer can elevate the rate of DNA unwinding, thus that of AceCas9 cleavage by use of a sgRNA containing a 24-nt spacer (FIG. 1A). The single-turnover rate of cleavage indeed increased by four times ($k_{cleavage}$=1.04±0.03 min$^{-1}$) of that with the sgRNA containing the 20-nt spacer ($k_{cleavage}$=0.26±0.02 min$^{-1}$) (FIG. 4D). This result shows that increased spacer-protospacer pairing, from 20-nt to 24-nt, improves the overall DNA cleavage efficiency. Note that the pseudo-first order rate constant of AceCas9 with the 24-nt spacer sgRNA is comparable to that of SpyCas9 on plasmid DNA substrates measured at 37° C. ($k_{cleavage}$=0.89±0.12 min$^{-1}$)[2].

AceCas9 Cleaves Negatively Supercoiled DNA Efficiently

Comparison of the cleavage rate for dsDNA oligo to that for the plasmid substrate showed that AceCas9 prefers plasmid DNA. To examine if it is simply the length of DNA substrate, which could facilitate one-dimensional diffusion, that accelerated the rate of cleavage for the plasmid DNA, cleavage kinetics were carried out on the same plasmid pre-treated with BamHI by use of the 20-nt spacer sgRNA (FIG. 4C). Surprisingly, the rate constant of linearized 3-kb DNA ($k_{cleavage}$=0.10±0.01 min$^{-1}$) was very similar to that of dsDNA oligo ($k_{cleavage}$=0.104±0.005 min$^{-1}$), thereby ruling out one-dimensional diffusion as the possible cause for the observed difference between oligo and plasmid DNA. Instead, the negative supercoil in the circular DNA acts as a favorable factor for AceCas9 function. To further explore the dependence of AceCas9 on DNA topology, the number of topoisomers of the pUC19 substrate was increased by treating it with E. coli gyrase before performing single turnover kinetics with AceCas9. The gyrase-treated plasmid (FIG.

4C) indeed resulted in faster rate of cleavage ($k_{cleavage}$=0.30±0.02 min$^{-1}$) than the untreated plasmid (FIG. 4C and Table 1). A similar rate difference when cleaving the supercoiled and linearized DNA plasmid by AceCas9 with the 24-nt guide sgRNA was observed, indicating DNA topology plays the same role in substrate binding when the guide region is extended (Table 1).

AceCas9 has Low Off-Target Cleavage Activity for Relaxed DNA

Figure 5B:
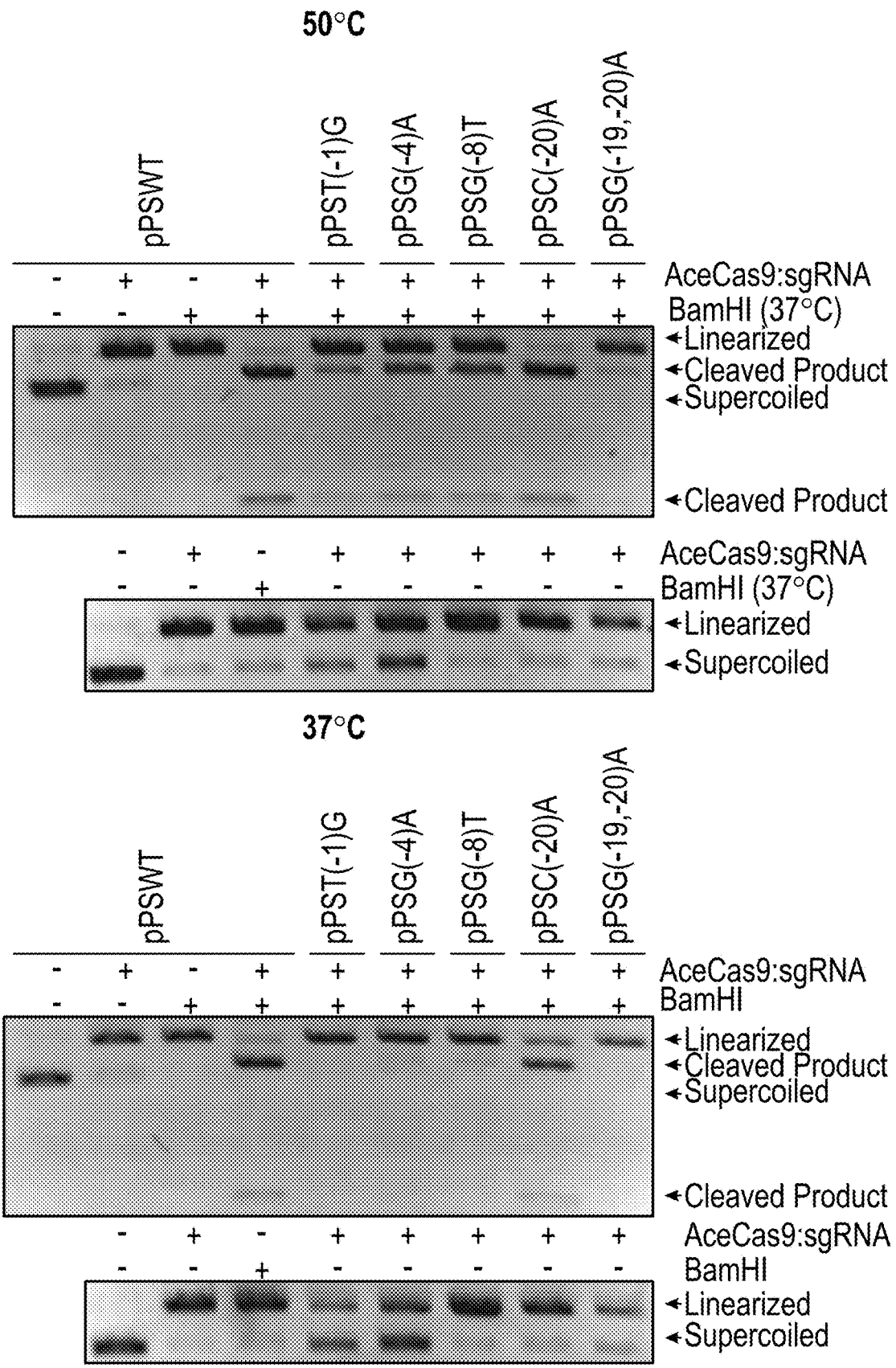
Figure 5C:
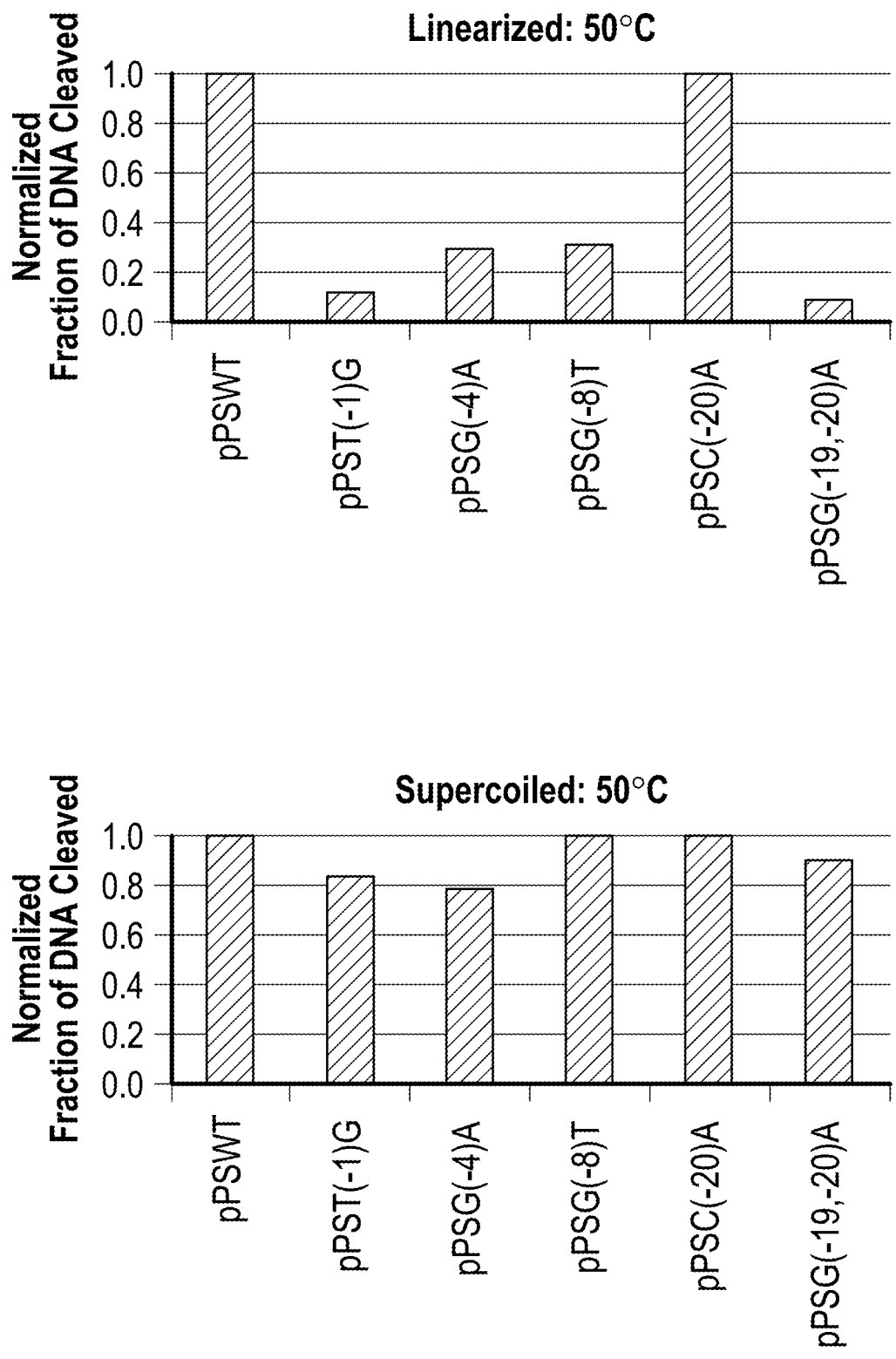
Figure 5C:
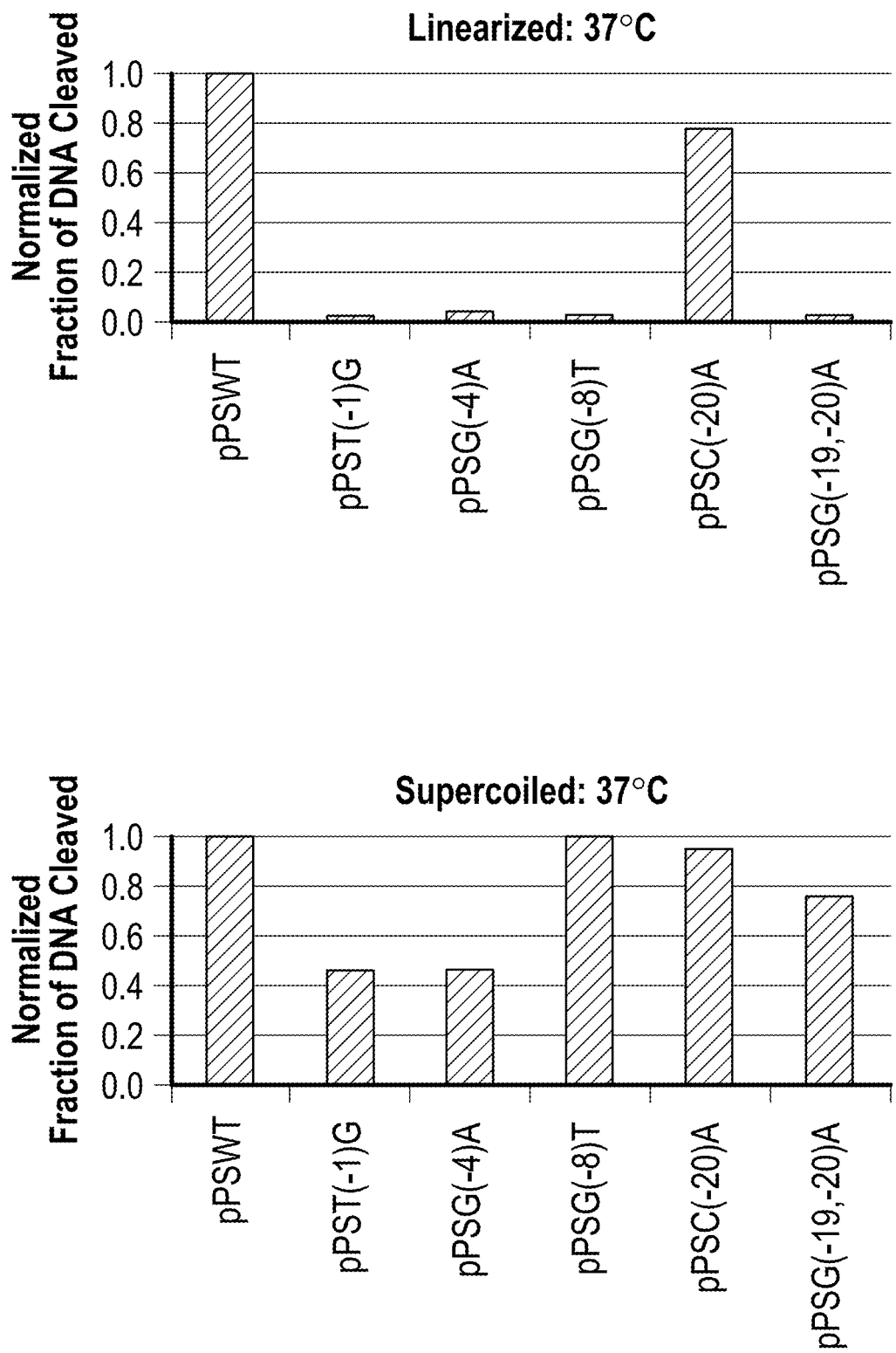

To investigate the specificity of AceCas9 for the protospacer, single or double mutations at positions −1, −4, −8, −19 and −20 of the protospacer were generated, and these plasmids were subjected to AceCas9 cleavage with the 20-nt spacer sgRNA (FIG. 5A). The fraction cleaved at the end of one hour incubation of AceCas9:sgRNA with each plasmid was quantified (FIG. 5B), and this value was compared to that of the wild-type plasmid (FIG. 5C). At 50° C. where AceCas9 activity is optimal, all plasmid mutants but position −4, pPSG(−4)A, were cleaved nearly to completion (FIGS. 5B and 5C). The pPSG(−4)A was cleaved poorly, reflecting the important role of position −4 and possibly its surrounding in substrate recognition by AceCas9. The similar pattern of cleavage activity was observed when the reaction temperature was lowered to 37° C. (FIG. 5C), despite an overall reduction in AceCas9 activity (FIG. 5B). Significantly, when these mutant plasmids were pre-linearized with BamHI, in which case, the wild-type plasmid had reduced cleavage (FIG. 5B), all mutations, except that at −20, resulted in detectable cleavage after reacting with molar excessive AceCas9 at both 50° C. and 37° C. (FIG. 5B). The shift in cleavage specificity is the most pronounced for position −1 where DNA unwinding occurs (FIGS. 5B and 5C), indicating that the energy stored in supercoiling helps to drive the initial steps of R-loop formation.

AceCas9 Cleaves DNA Efficiently in *Escherichia coli*

Figure 6A:
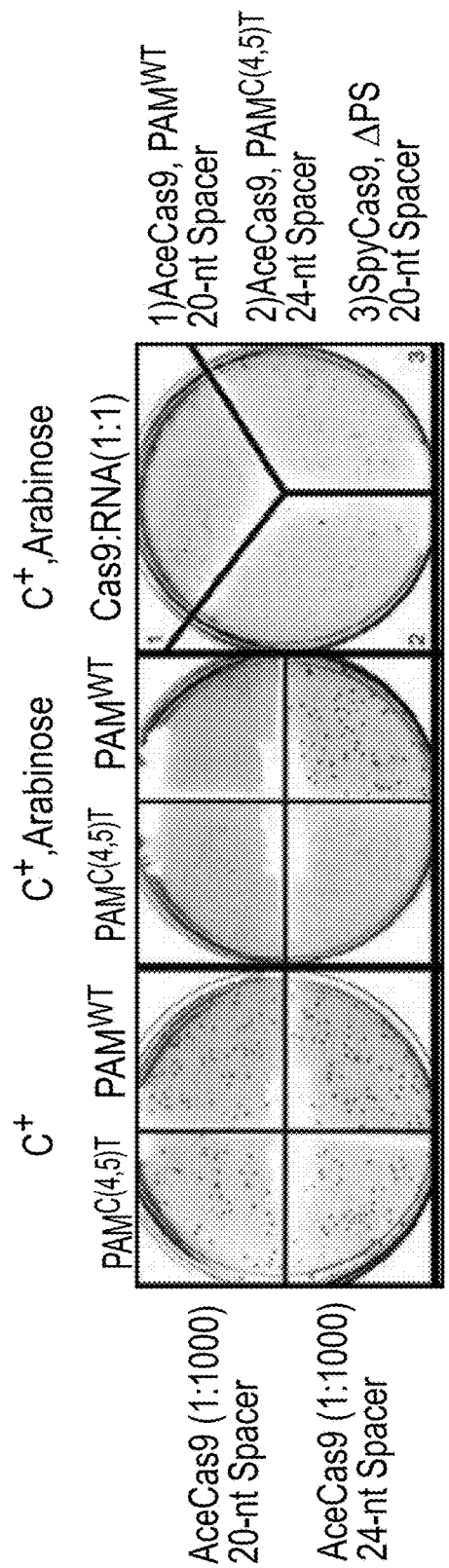
FIGS. 6A-6C. In vivo Activity of AceCas9.
Figure 6B:
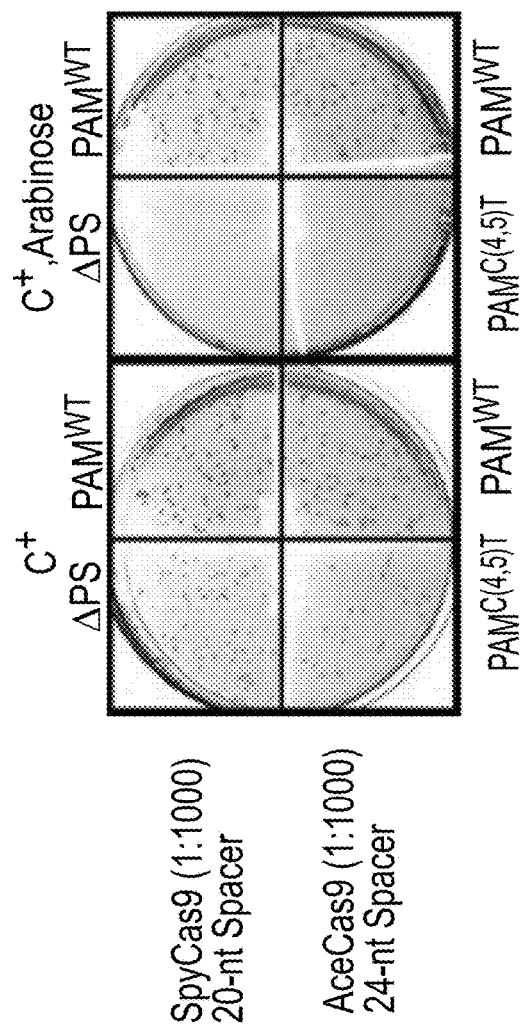
Figure 6C:
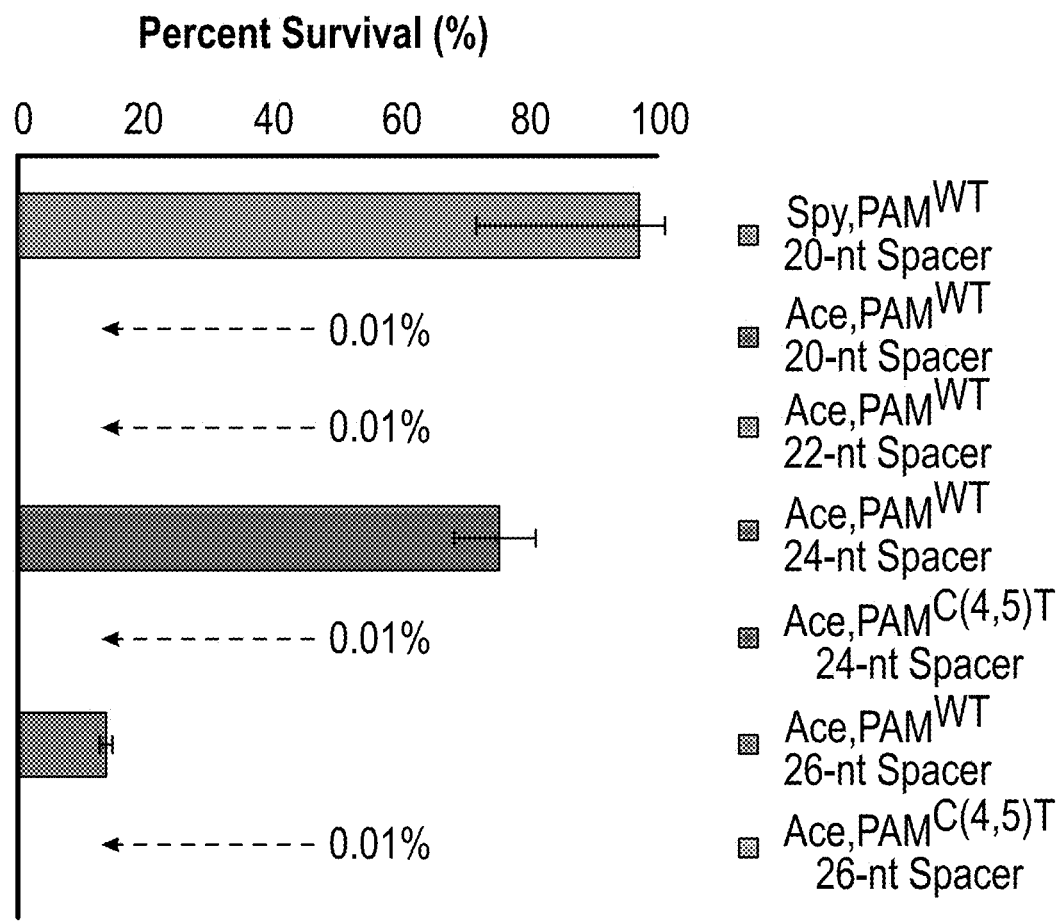

To confirm the DNA cleavage activity by AceCas9 under in vivo condition, a bacteria-based cell survival assay was performed (FIGS. 6A-6C). The plasmid co-expressing AceCas9 (or SpyCas9) and its sgRNA was transformed into *E. coli* competent cells harboring a target (selection) plasmid that expresses the toxic ccdB gene under the control of BAD promoter (inducible with arabinose). Successful cleavage of the ccdB plasmid by Cas9 would render the growth of *E. coli* cells when induced by arabinose (FIGS. 6A and 6B). The efficiency of DNA cleavage in *E. coli* could thus be measured as the percentage of colonies with arabinose versus those without arabinose. As expected, the cells transformed with SpyCas9 and its sgRNA targeting ccdB have about 96% survival (FIG. 6C). The cells transformed with AceCas9 and its 24-nt spacer sgRNA also reached nearly 75% survived. Strikingly, cells transformed with AceCas9 and the 20-nt or a 22-nt spacer sgRNA had less than 0.01% survival (FIG. 6C), reflecting the lower rate of cleavage for the 20-nt spacer sgRNA in vitro. Further extension of the spacer length to 26-nt resulted in about 14% cell survival but did not improve cleavage efficiency (FIG. 6C).

An experiment was conducted in *E. coli* to see if the 5'-NNNCC-3' PAM is specifically recognized by AceCas9, and this experiment was conducted by carrying out the survival assay with the ccdB plasmid containing a 5'-NNNTT-3' PAM in place of a 5'-NNNCC-3' PAM. Nearly no survival colonies (<0.001% survival) were observed under the conditions used for the wild-type target (FIGS. 6A and 6C), confirming that 5'-NNNCC-3' is a functional PAM for AceCas9 in *E. coli* cells.

DISCUSSION

Currently known Cas9 substrates require a guanine-containing adjacent motif to be cleaved. Those for AceCas9, in contrast, are associated with a cytosine adjacent motif. Mutational studies indicated that AceCas9 is highly specific for cytosine at position 4 or 5 under a variety of conditions. This specificity for PAM is unprecedented, as other Cas9s tolerated mutation to similar nucleotides (i.e. G to A for SpyCas9), and can thus be used for applications requiring targeting cytosine adjacent DNA. AceCas9 differs from another type II-C Cas9, NmCas9, and resembles type II-A SpyCas9 in that it does not require a fully base paired PAM region, indicating that the interaction between the PAM and the PID of Cas9 are, in general, diverse and potentially species—rather than subtype-specific.

The kinetic analysis revealed a unique dependence of AceCas9 on negatively supercoiled DNA. The fact that dsDNA was cleaved more slowly than ssDNA suggests that DNA unwinding is the rate-limiting step for AceCas9. Consistently, the rate of cleavage increased when the first protospacer base pair was disrupted. AceCas9 is able to lower the energetic barrier of DNA unwinding by harnessing the energy stored in DNA topology, as its rate of cleavage for a supercoiled plasmid DNA is about 2.6-fold that for a linearized plasmid DNA or a dsDNA oligo. Unwinding circular DNA introduces positive supercoiling, and thus strains in the DNA double helix structure. Negative supercoiling allows faster duplex rotation resulting from the superhelical torque, thereby alleviating the structural strain during unwinding and providing a favorable energy for AceCas9 to reach its final conformation for catalysis.

The bacteria-based positive-selection assay results further support the findings that an elongated spacer improves the catalytic activity of AceCas9 due to its role in unwinding dsDNA. The measured DNA cleavage efficiency in *E. coli* agrees with the rate of cleavage obtained in vitro. The 4-fold rate increase of the 24-nt spacer from that of the 20-spacer guided AceCas9 is translated into a more than 12,500-fold increase in DNA cleavage efficiency in cells. The narrow dependence of AceCas9 on the 24-nt spacer sgRNA provides an opportunity to improve the off-target activities of Cas9-derived tools.

The dependence of AceCas9 activity on DNA topology has not been detected for other characterized Cas9s. However, this effect was observed for Cascade, a type I-E CRISPR-Cas system and for SpyCas9 in cleaving an artificial plasmid containing consecutive targets. For a typical single target plasmid, cleavage of plasmids by SpyCas9 has a compatible if not slightly lower rate constant than that of oligo dsDNA. This indicates a mechanistic distinction between the more sophisticated type II-A Cas9 and the simpler type II-C Cas9. The type II-A Cas9 can be able to keep the effect of DNA unwinding localized, while the type II-C allows it to spread along the DNA molecule in order to take advantage of energy stored in DNA topology.

Significantly, the biochemical data showed that AceCas9 exhibits high specificity for the protospacer on relaxed DNA. Whereas several mutations of the protospacer within a supercoiled plasmid were largely tolerated by AceCas9, those within its pre-linearized counterpart were not. The disparate activity on different DNA topologies is especially striking for the first base pair of the protospacer, where DNA unwinding and target-sgRNA pairing are initiated. This indicates that negative supercoiling in the plasmid specifically enhances these steps. The absence of favorable superhelicity in pre-linearized DNA renders AceCas9 unable to overcome mismatches between the DNA and the sgRNA in the PAM proximal region. This property of AceCas9 makes it applicable to chromatin domain specific editing.

AceCas9 is functional in vitro at 25° C. through 60° C. with activity being optimal at elevated temperatures. A low temperature environment can increase specificity of Ace-Cas9. The in vitro cleavage experiments indeed provided some evidence that AceCas9 is less tolerant to mutations within the protospacer at 37° C. than at 50° C. Additionally, temperature alone or in combination with DNA topology can be used to control AceCas9 specificity in vivo.

Experimental Procedures

Cloning of AceCas9 and AceCas9 Mutant

*A.cellulolyticus* cas9 gene fused at the 3' end with the sequence encoding a hexahistidine tag (SEQ ID NO: 1) was PCR-amplified from the genomic DNA of *Acidothermus cellulolyticus* strain 11B (ATCC 43068D-5) and cloned into pET28b (Novagen) to yield pETAceCas9. The H591A mutant of *A.cellulolyticus* cas9 gene was generated by site-directed mutagenesis kit Q5 (New England Biolabs) using appropriate primers purchased from IDT DNA and Eurofins Genomics. The clones encoding Cas9 and its H591A mutant were verified by Sanger sequencing (Eurofins Genomics).

Protein Expression and Purification

*E. coli* Rosetta (DE3) cells transformed with pETAceCas9 were grown in LB medium with appropriate antibiotics until $OD_{600}$ reached 0.4-0.6 before induction by 0.3 mM Isopropyl β-D-1-thiogalactopyranoside (IPTG) followed by continued incubation at 16.5° C. for 18 hours. Cells were harvested by centrifugation at 4250 rpm for 30 minutes, resuspended in a lysis buffer (50 mM Tris pH 8.0, 1 M NaCl, 1 mM imidazole pH 8.0, 10% glycerol, 14.3 mM (3-mercaptoethanol [βME] and 0.3 mM phenylmethylsulfonyl fluoride [PMSF]), and lysed by sonication. The lysate was clarified by centrifugation at 22,000 rpm at 4° C. for 30 minutes and the cleared supernatant was passed through a Ni-NTA agarose column equilibrated with the lysis buffer. The column was washed by 15-20 column volumes of the lysis buffer, followed by another 15-20 column volumes of a wash buffer (30 mM Tris pH 8.0, 250 mM NaCl, 5 mM imidazole pH 8.0, 5% glycerol). AceCas9 was eluted by an elution buffer that contained 30 mM Tris pH 8.0, 150 mM NaCl, 350 mM imidazole pH 8.0, 5% glycerol. To remove nucleic acids that associated with AceCas9, the Ni-NTA elutant was loaded into an HiTrap Heparin HP (GE Healthcare) column equilibrated with an ion exchange buffer (30 mM Tris pH 7.5, 100 mM KCl, 5% glycerol, 14.3 mM βME), and eluted with a linear salt gradient. Heparin column elutant was concentrated and then loaded on to a size-exclusion column HiLoad 26/60 Superdex 200 (GE Healthcare) equilibrated with a gel filtration buffer (30 mM HEPES pH 7.5, 200 mM KCl, 14.3 mM βME). The peak fractions were concentrated and buffer exchanged to a storage buffer (30 mM HEPES pH 7.5, 200 mM KCl, 10 mM (Tris(2-carboxyethyl)phosphine) [TCEP]) using Amicon Ultra-15 Centrifugal Filter Units (Millipore), prior to being flash frozen in liquid nitrogen and stored at −80° C. Expression and purification of AceCas9 mutant followed the same procedure.

In Vitro Transcription and Purification of sgRNA

400 μM of an oligo with T7 promoter sequence was annealed in equimolar with a DNA oligo that encodes the reverse complement sequence of sgRNA fused with that of T7 promoter (Table 3) in a 10×PCR buffer at 94° C. for 4 minutes followed by slow cooling. The sgRNA was synthesized by in vitro transcription by adding 1 μM of annealed dsDNA template into 50 mM Tris-HCl pH 8.0, 40 mM $MgCl_2$, 10 mM dithiothreitol (DTT), 2 mM spermidine, 5 mM ATP pH 8, 5 mM UTP pH 8, 6.2 mM CTP pH 8, 6.2 mM GTP pH 8, 0.1% Triton X-100, and 0.15 mg/mL T7 RNA polymerase. The transcription reaction was incubated at 37° C. water bath overnight, and quenched by addition of EDTA to a final concentration at 65 mM. The sgRNA was extracted by phenol:chloroform extraction, and purified by either ethanol precipitation or size exclusion chromatography (HiLoad Superdex 75 16/60, GE Healthcare) at 4° C. in 20 mM Tris pH 7.4, 150 mM KCl. The concentration was determined by 260 nm absorption using an ND-1000 spectrophotometer (NanoDrop). When needed, sgRNA was concentrated by Vivaspin 20 (Sartorius) before being stored at −80° C.

PAM Library Construction

A pre-determined protospacer sequence followed by 7-bp degenerate sequences (Table 3) was cloned into the high copy number plasmid pUC19 vector ~500-bp upstream of the BamHI cleavage site. The plasmid library was transformed into chemical competent *E. coli* DH5a cells by standard heat shock transformation procedure and incubated in LB agar plates containing 75 μg/mL ampicillin. More than 500 single colonies were picked and pooled for growth in fresh LB medium in the presence of ampicillin prior to DNA extraction. Sequences of the extracted DNA library plasmids were verified by Sanger sequencing (Eurofins Genomics) using the standard M13 forward and M13 reverse sequencing to ensure the presence of the 7-bp degenerate region. To cleave the DNA library, 300 ng of plasmid DNA library was incubated with pre-annealed 1 μM AceCas9 and 5 μM sgRNA in a 20 pt volume containing a cleavage buffer (20 mM Tris pH 7.5, 150 mM KCl, 2 mM DTT, 10 mM $MgCl_2$, 5% Glycerol) at 37° C. for 1.5 hours. 44 units (2.2 μL of 20000 U/mL) of BamHI (or Sbfl) was then added to the reaction at 37° C. and incubated for an additional 1.5 hours. The reaction was stopped by the addition of EDTA to a final concentration of 50 mM and 6×NEB Purple Loading dye before being resolved on a 1% 0.8×TAE agarose gel. The cleavage product that contained the PAM sequence was gel extracted by E.Z.N.A. gel extraction kit (Omega Bio-tek), end repaired and ligated with index primers using NEB Ultra II Library Prep Kit and NEBNext Multiplex Oligos for Illumina (New England Biolabs). The treated fragments were amplified by PCR and subsequently cloned into pCR4Blunt-TOPO vector (Thermo Fisher Scientific). 34 independent clones were subjected to Sanger sequencing using the standard T3 and T7 primers. Sequences with the inserted PCR product, which contains parts of the protospacer sequence and the 7-bp degenerate region, were identified based on pUC19 backbone sequence downstream of library sequence. The region composed of 7-bp of the PAM sequence and 15-bp neighboring sequences in both directions was extracted and aligned using WebLogo.

Oligonucleotide DNA Cleavage Assay

Single stranded oligonucleotide DNAs or those containing HEX- or 6-FAM-labels were purchased from Eurofins Genomics or IDT (Table 3). The labeled DNA strand was annealed with a non-label strand in a 1:20 (HEX) or 1:1.2 (6-FAM) molar ratio at 75° C. for 5 minutes, followed by slow cooling to room temperature to generate dsDNA. For cleavage, 500 nM AceCas9 was pre-incubated with equimolar of sgRNA in a cleavage buffer for 15 minutes at 37° C. and cooled to room temperature. The ssDNA or dsDNA substrates were then added to the tube to a final concentration 3 nM to initiate the reaction. The reaction tube was incubated for 1 hour at 50° C., before being stopped by the addition of 2× formamide gel loading buffer (90% formamide, 50 mM EDTA pH 8.0). The samples were heated at ~90° C. for 2 minutes prior being resolved on a 15% urea denaturing polyacrylamide (19:1) TBE gel. The gel was scanned and visualized by Typhoon Trio (GE Healthcare) using appropriate filters/excitation wavelengths.

Plasmid DNA Cleavage Assay

The same protospacer as that in the dsDNA and PAM were introduced into pUC19 to construct the plasmid substrate for AceCas9 (Table 3). For cleavage reaction, 100 ng (~6 nM) of plasmid DNA was incubated with pre-annealed 500 nM AceCas9:sgRNA in a cleavage buffer at 50° C. for 1 hour. The reaction was quenched by the addition of 5× gel loading buffer (25 mM Tris pH 7.5, 250 mM EDTA pH 8, 1% SDS, 0.05% w/v bromophenol blue, 30% glycerol) and resolved on a 0.5% 1×TBE agarose gel with EZ-Vision In-Gel solution (Amresco). To test metal requirements, 10 mM $MgCl_2$ in regular cleavage buffer was replaced by the following divalent salts: $MnCl_2$, $CuCl_2$, $NiCl_2$, $CdCl_2$, $CaCl_2$, $CoCl_2$, $ZnCl_2$, $BaCl_2$. The gels were imaged by ChemiDoc XRS System (Bio-Rad) and analyzed by ImageQuant (GE Healthcare).

Generation of Negatively Supercoiled DNA by DNA Gyrase

To create a more negatively supercoiled DNA for single-turnover kinetic assay, DNA gyrase from *E. coli* (NEB) was used. Briefly, 1 μL gyrase was added to 1 μg of plasmid DNA in 30 μl 1× manufacture supplied buffer (NEB) and the mixture was incubation in a 37° C. water bath for 30 minutes. The gyrase-treated DNA was then purified by ethanol precipitation and resuspeneded in $ddH_2O$. To confirm its superhelicity, the plasmid is resolved in a 0.5% 1×TBE agarose gel (with final concentration of 10 μg/mL chloroquine from Sigma-Aldrich) and stained with SYBR Gold (Thermo Fisher Scientific) for 30 minutes before visualized by ChemiDoc XRS System (Bio-Rad).

Single-Turnover Kinetic Assay

For kinetic assays with oligonucleotides, 500 nM AceCas9 sgRNP was pre-annealed in the presence of a cleavage buffer in a master mix for triplicate reactions at 37° C. for 15 minutes, then cooled down on ice before adding ice cold, HEX-labeled dsDNA (final concentration at 3 nM). The reaction mixture was aliquoted into 33 pre-chilled Eppendorf tubes on ice and then quickly transferred to a 50° C. water bath to initiate reactions. Samples were removed in triplicate and placed on ice at each time point. To ensure reactions were quenched thoroughly, pre-chilled 2× formamide gel loading buffer was added to each tube immediately afterwards. At the end of the reaction, samples were mixed and heated at ~90° C. for 2 minutes before being loaded to a 15% urea denaturing polyacrylamide gel. The gel was scanned by Typhoon Trio (GE Healthcare) using green laser at 532 nm with 520-nm band pass filter. Intensities of the bands corresponding to uncleaved and cleaved DNA were integrated using the ImageQuant TL software (GE Healthcare) and were fitted to a simple exponential progress curve using Prism 6 (GraphPad Software) to extract $k_{cleavage}$.

Kinetic assays with DNA plasmids followed the same procedure with the following modifications. ~3.6 μg (~6 nM) of plasmid DNA was added to the pre-annealed AceCas9:sgRNA, mixed, and aliquoted into pre-chilled Eppendorf tubes on ice before initiating reactions. Reactions were quenched by the addition of 5× gel loading buffer immediately after placing tubes on ice. Samples were loaded directly into a 0.5% 1×TBE agarose gel with EZ-Vision In-Gel solution (Amresco) and resolved at 6.5 mA/cm for ~1 hour. The gel was scanned by ChemiDoc XRS System (Bio-Rad), analyzed by ImageQuant (GE Healthcare) and were fitted to a simple exponential progress curve using Prism 6 (GraphPad Software) to extract $k_{cleavage}$.

Bacteria-Based Positive Selection Assay

The bacteria-based positive selection assay was performed as previously described with minor modifications. Briefly, a positive selection plasmid encoding ccdB toxin was isolated and mutagenized to contain a target site with PAM and variants by Q5 SDM kit (NEB). Each selection plasmid variant was transformed into *E. coli* BW25141 (λDE3) cells and made competent for electroporation. A co-expression plasmid for AceCas9 and its sgRNA was constructed by inserting AceCas9 and sgRNA encoding genes into the multiple cloning sites of the pCACYduet vector. ~100 ng of AceCas9:sgRNA co-expression plasmid (or its variants) were transformed into the ccdB-harboring cells by electroporation. Cells were recovered in 500 μL of SOB media and shake at ~250 rpm for 5 minutes at 37° C., before being diluted 5-fold with SOB media and further incubated for 60 minutes. Harvested culture were further diluted ~1000-fold (or no dilution for controls) and plated on various agar plates. Experiment with SpyCas9 was performed as above by use of a modified BPK764 plasmid (Addgene plasmid #65767 deposited by Keith Joung).

Tables

Table 1 shows the rate constant of AceCas9 cleaving various substrates. Table 2 shows a list of reported PAM sequences for Cas9 orthologs. Table 3 shows a list of oligos DNA used in this disclosure.

TABLE 1

Rate constant of AceCas9 cleaving various substrates.

| Substrate | Rate constant $(min^{-1})$ | S.D.* $(min^{-1})$ | Goodness of Fit (R Square) |
|---|---|---|---|
| 20-nt Spacer sgRNA | | | |
| dsDNA + PAM | 0.104 | 0.005 | 0.9852 |
| T(−1)C bulge dsDNA + PAM | 0.179 | 0.007 | 0.9904 |
| T(−1)C bulge dsDNA − PAM | 0.098 | 0.009 | 0.9349 |
| ssDNA | 0.65 | 0.10 | 0.8348 |
| Supercoiled DNA plasmid (37° C.) | 0.093 | 0.003 | 0.9950 |
| Supercoiled DNA plasmid (50° C.) | 0.26 | 0.02 | 0.9761 |
| Gyrase-treated supercoiled DNA plasmid (50° C.) | 0.30 | 0.02 | 0.9649 |
| BamHI-treated linearized DNA plasmid (50° C.) | 0.10 | 0.01 | 0.9484 |
| 24-nt Spacer sgRNA | | | |
| Supercoiled DNA plasmid (37° C.) | 0.28 | 0.01 | 0.9538 |
| Supercoiled DNA plasmid (50° C.) | 1.04 | 0.03 | 0.9684 |
| BamHI-treated linearized DNA plasmid (50° C.) | 0.53 | 0.05 | 0.9798 |

*S.D. denotes standard deviation of experiments in triplicate

TABLE 2

List of Reported PAM Sequences for Cas9 orthologs.

| Organism (locus) | PAM Sequence | Type | Publication |
|---|---|---|---|
| Lactobacillus buchneri | NAAAAN | 2-A | Anders et al., 2014 |
| Listeria innocua | NGG | 2-A | Anders et al., 2014 |

TABLE 2-continued

List of Reported PAM Sequences for Cas9 orthologs.

| Organism (locus) | PAM Sequence | Type | Publication |
|---|---|---|---|
| *Streptococcus agalactiae* | NGG | 2-A | Lopez-Sanchez et al., 2012 |
| *Streptococcus aureus* | NNGRRNN | 2-A | Ran et al., 2015 |
| *Streptococcus mutans* | NGG | 2-A | Fonfara et al., 2014 |
| *Streptococcus pasteurianus* | NNGTGAN | 2-A | Ran et al., 2015 |
| *Streptococcus pyogenes* | NGG | 2-A | Jinek et al., 2012 |
| *Streptococcus pyogenes* | NAG | 2-A | Mali et al., 2013 |
| *Streptococcus thermophilus* (CRISPR1) | NNAGAA | 2-A | Deveau et al., 2008 |
| *S. thermophilus* (CRISPR1) | NNAGAAW | 2-A | Horvath et al., 2008 |
| *S. thermophilus* (CRISPR1) | NNAAAAW | 2-A | Fonfara et al., 2014 |
| *Streptococcus thermophilus* (CRISPR3) | NGGNG | 2-A | Gasiunas et al., 2012 |
| *S. thermophilus* (CRISPR3) | NGG | 2-A | Fonfara et al., 2014 |
| *Treponema denticola* | NAAAAN | 2-A | Esvelt et al., 2013 |
| *Francisella novicida* | NG | 2-B | Fonfara et al., 2014 |
| *Acidothermus cellulolyticus* | NNNCC | 2-C | This study |
| *Brevibacillus laterosporus* | NNNNCND | 2-C | Karvelis et al., 2015 |
| *Campylobacter jejuni* | NNNNACA | 2-C | Fonfara et al., 2014 |
| *Campylobacter lari* | NNGGGNN | 2-C | Ran et al., 2015 |
| *Corynebacterium diphtheriae* | NGGNNNN | 2-C | Ran et al., 2015 |
| *Neisseria cinerea* | NNNNGAT | 2-C | Ran et al., 2015 |
| *Neisseria meningitidis* | NNNNGATT | 2-C | Zhang et al., 2013 |
| *Parvibaculum lavamentivorans* | NNNCAT | 2-C | Ran et al., 2015 |
| *Pasteurella multocida* | GNNNCNNA | 2-C | Fonfara et al., 2014 |

TABLE 3

List of oligos DNA used in this disclosure.

| Name (Purpose) | Identification | Sequence | SEQ ID NO |
|---|---|---|---|
| 20-nt Spacer sgRNA DNA Template (for in vitro transcription) | Top Strand | 5'-_TAATACGACTCACTATA_-3' | 2 |
| | Bottom Strand | 5'-GAACCCCTCGCTGCTGCGAGGGGGTGAAGAA TGCGACCCCACGAAGGGGTCTTGCTAGGTAGCC TTTTCAGGCTCCCCAGCataccaggatcttgccatcc_T ATAGT GAGTCGTATTA_-3' | 3 |
| 24-nt Spacer sgRNA DNA Template (for in vitro transcription) | Bottom Strand | 5'-GAACCCCTCGCTGCTGCGAGGGGGTGAAGAA TGCGACCCCACGAAGGGGTCTTGCTAGGTAGCC TTTTCAGGCTCCCCAGCataccaggatcttgccatccta cc_TAT AGTGAGTCGTATTA_ -3' | 4 |

TABLE 3-continued

List of oligos DNA used in this disclosure.

| Name (Purpose) | Identification | Sequence | SEQ ID NO |
|---|---|---|---|
| Q5 Site-directed Mutagenesis Primers (Generation of PAM Library) | Forward | 5'-TAAGAAACCATTATTATCATGACATTAACCTATAAA-3' | 5 |
| | Reverse | 5'-NNNNNNNataccaggatcttgccatccGACGTCAGGTGGCACTTTTCG-3' | 6 |
| Q5 SDM Primers (Generation of of PAM$^{WT}$) | Forward | 5'-tcctggtatACACCaagcttGGCTGTTTTGGCGGATG-3' | 7 |
| | Reverse | 5'-tcttgccatcctacctctagaGCGTGATATTACCCTGTTATC-3' | 8 |
| Q5 SDM Primers (Generation of PAM$^{C(4,5)T}$) | Reverse | 5'-tcctggtatACATTaagcttGGCTGTTTTGGCGGATG-3' | 9 |
| Q5 SDM Primers (Generation of 22-nt Spacer sgRNA) | Forward | 5'-GGTGGCTGAGATCAGCCACTTCGCTGGGGAGC CTGAAAAG-3' | 10 |
| | Reverse | 5'-TATAGTGAGTCGTATTAATTTCGATTATGCGGC-3' | 11 |
| Q5 SDM Primers (Generation of 24-nt Spacer sgRNA) | Forward | 5'-GGTAggatggcaagatcctggtatGC-3' | 12 |
| Q5 SDM Primers (Generation of 26-nt Spacer sgRNA) | Forward | 5'-ggcggcagtagcgcggtggtcccaccGCTGGGGAGCCTGA AAAG-3' | 13 |
| Sequencing primers (PAM Library, Plasmid DNA cleavage) | Forward | 5'-CTTTCACCAGCGTTTCTGGGTGA-3' | 14 |
| | Reverse | 5'-GCCTGAATGGCGAATGGCGCCTG-3' | 15 |
| Sequencing primers (PAM$^{WT}$, pAm$^{C(4,5)T}$) | Forward | 5'-GGCCAGTGCACGTCTGCTGTC-3' | 16 |
| | Reverse | 5'-CGGATTTGTCCTACTCAGGAGAGCG-3' | 17 |
| WT (oligo cleavage assay, kinetic analysis) | Non-targeting Targeting | 5'-ggatggcaagatcctggtatCCACCTTAGC-3' 3'-cctaccgttctaggaccataGGTGGAATCG-HEX-5' | 18 19 |
| PAM-A3T (oligo cleavage assay) | Non-targeting† Targeting* | 5'-ggatggcaagatcctggtatCCTCCTTAGC-3' 3'-cctaccgttctaggaccataGGAGGAATCG-HEX-5' | 20 21 |
| PAM-C4G (oligo cleavage assay) | Non-targeting† Targeting* | 5'-ggatggcaagatcctggtatCCAGCTTAGC-3' 3'-cctaccgttctaggaccataGGTCGAATCG-HEX-5' | 22 23 |
| PAM-C5G (oligo cleavage assay) | Non-targeting† Targeting* | 5'-ggatggcaagatcctggtatCCACGTTAGC-3' 3'-cctaccgttctaggaccataGGTGCAATCG-HEX-5' | 24 25 |
| PAM-C4,5G* (oligo cleavage assay) | Non-targeting† | 5'-ggatggcaagatcctggtatCCAGGTTAGC-3' | 26 |
| PS-1.b (cleavage assay) | Non-targeting† | 5'-ggatggcaagatcctggtagCCACCTTAGC-3' | 27 |
| PAM-X (oligo cleavage assay, kinetic analysis) | Non-targeting† Targeting* | 5'-ggatggcaagatcctggtatGATTCACAGC-3' 3'-cctaccgttctaggaccataCTAAGTGTCG-HEX-5' | 28 29 |
| PS-1.bX (cleavage assay, kinetic analysis) | Non-targeting† | 5'-ggatggcaagatcctggtacGATTCACAGC-3' | 30 |
| WT2 (oligo cleavage assay) | Non-targeting Targeting | 5'-GGTAggatggcaagatcctggtatGATCCTGTGC-FAM-3' 3'-CCATcctaccgttctaggaccataCTAGGACACG-5' | 31 32 |

TABLE 3-continued

List of oligos DNA used in this disclosure.

| Name (Purpose) | Identification | Sequence | SEQ ID NO |
|---|---|---|---|
| PAM-G(4,5)C* (oligo cleavage assay) | Targeting* | 3'-CCATcctaccgttctaggaccataCTACCACACG-5' | 33 |
| pPAM-C4T (Q5 Primers) | Forward | 5'-TAAGAAACCATTATTATCATGACATTAAC-3' | 34 |
| | Reverse | 5'-AT<u>GATGT</u>ataccaggatcttg-3' | 35 |
| pPAM-C5T (Q5 Primer) | Reverse | 5'-AT<u>AGTGT</u>ataccaggatcttg-3' | 36 |
| pPAM-C4,5T (Q5 Primer) | Reverse | 5'-AT<u>AATGT</u>ataccaggatcttg-3' | 37 |
| pPAM-C4G (Q5 Primer) | Reverse | 5'-AT<u>GCTGT</u>ataccaggatcttg-3' | 38 |
| pPAM-c5G (Q5 Primer) | Reverse | 5'-AT<u>CGTGT</u>ataccaggatcttg-3' | 39 |
| pPAM-C4,5G (Q5 Primer) | Reverse | 5'-AT<u>CCTGT</u>ataccaggatcttg-3' | 40 |
| pPST(-1)G (Q5 Primer) | Reverse | 5'-AT<u>GGTGT</u>ctaccaggatcttg-3' | 41 |
| pPSWT (Q5 Primers) | Forward | 5'-GGTAggatggcaagatcctggtat<u>AC</u>-3' | 42 |
| | Reverse | 5'-GACGTCAGGTGGCACTTTT-3' | 43 |
| pPSG(-4)A (Q5 Primer) | Forward | 5'-GGTAggatggcaagatcctgatat<u>ACACC</u>-3' | 44 |
| pPSC(-8)T (Q5 Primer) | Forward | 5'-GGTAggatggcaagattctggtat<u>ACACC</u>-3' | 45 |
| pPSG(-20)A (Q5 Primer) | Forward | 5'-GGTAagatggcaagatcctggtat<u>ACACC</u>-3' | 46 |
| pPSG(-19,-20)A (Q5 Primer) | Forward | 5'-GGTAaaatggcaagatcctggtat<u>A</u>-3' | 47 |
| Spacer Oligos for BPK764 (Generation of SpyCas9 sgRNA targeting positive-selection plasmid) | Forward | 5'-ATAGGAGGTAggatggcaagatcctgg-3' | 48 |
| | Reverse | 5'-AAACccaggatcttgccatccTACCTC-3' | 49 |

*Italic and underline*, T7 promoter sequence; bold and underline, tetraloop; <u>underlined</u>, PAM region; lower case, protospacer sequence; bold: mutation relative to WT sequence; asterisk(*), mutation on targeting DNA strand; double dagger(†), mutation on nontargeting DNA strand.

---

The invention claimed is:

1. A method for specifically manipulating nucleic acids in a cell comprising:
contacting the cell with a cytosine-specific Cas9 endonuclease and a single guide RNA (sgRNA) targeting a protospacer sequence of the nucleic acids that is adjacent to a Protospacer Adjacent Motif (PAM) sequence of the nucleic acids,
wherein the cytosine-specific Cas9 endonuclease is a Type II-C *Acidothermus cellulolyticus* Cas9 (Ace-Cas9).

2. The method of claim 1, wherein the PAM sequence is downstream of the protospacer sequence on a non-targeting strand of the nucleic acids.

3. The method of claim 2, wherein the PAM sequence is five nucleotides.

4. The method of claim 3, wherein the PAM sequence is 5'-NNNCC-3'.

5. The method of claim 1, wherein the sgRNA comprises an 18 to 26 nucleotide guide region complementary to the protospacer sequence.

6. The method of claim 1, wherein an ambient temperature of the cell is 25-60° C.

7. The method of claim 1, wherein an ambient temperature of the cell is 50-60° C.

8. The method of claim 1, wherein the nucleic acids are deoxyribonucleic acids.

9. The method of claim 1, wherein the nucleic acids are supercoiled or linearized.

10. The method of claim 1, wherein a plasmid comprises the nucleic acids.

11. The method of claim 1, wherein a chromosome comprises the nucleic acids.

12. The method of claim 1, wherein the cell is a bacterial cell, a fungal cell, an archaea cell, a plant cell, or an animal cell.

13. The method of claim 1, wherein contacting the cell with the cytosine-specific Cas9 endonuclease and the sgRNA introduces at least one nucleotide insertion and/or substitution in the nucleic acids.

14. The method of claim 13, wherein contacting the cell with the cytosine-specific Cas9 endonuclease and the sgRNA causes disruption of a protein-encoding gene of the nucleic acids.

15. The method of claim 13, further comprising contacting the cell with a desired nucleic acid repair template.

16. The method of claim 15, wherein contacting the cell with the cytosine-specific Cas9 endonuclease, the sgRNA, and the desired nucleic acid repair template causes: (i) disruption of a protein-encoding gene of the nucleic acids, (ii) replacement of the protein-encoding gene of the nucleic acids with a substitute gene, or (iii) introduction a new gene into the nucleic acids.

* * * * *

SEQUENCE LISTING

<160> NUMBER OF SEQ ID NOS: 103

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taatacgact cactata                                                    17

<210> SEQ ID NO 3
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3 gaacccctc gctgctgcga gggggtgaag aatgcgaccc cacgaagggg tcttgctagg      60
tagccttttc aggctcccca gcataccagg atcttgccat cctatagtga gtcgtatta     119

<210> SEQ ID NO 4
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4 gaacccctc gctgctgcga gggggtgaag aatgcgaccc cacgaagggg tcttgctagg      60
tagccttttc aggctcccca gcataccagg atcttgccat cctacctata gtgagtcgta    120
tta                                                                  123

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taagaaacca ttattatcat gacattaacc tataaa                               36

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(7)
<223> OTHER INFORMATION: a, c, t, g, unknown or other

<400> SEQUENCE: 6
nnnnnnnata ccaggatctt gccatccgac gtcaggtggc acttttcg                  48

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcctggtata caccaagctt ggctgttttg gcggatg                              37

<210> SEQ ID NO 8
<211> LENGTH: 42
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 8
tcttgccatc ctacctctag agcgtgatat taccctgtta tc                          42

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcctggtata cattaagctt ggctgttttg gcggatg                                37

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtggctgag atcagccact tcgctgggga gcctgaaaag                             40

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatagtgagt cgtattaatt tcgattatgc ggc                                    33

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtaggatgg caagatcctg gtatgc                                            26

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcggcagta gcgcggtggt cccaccgctg gggagcctga aaag                        44

<210> SEQ ID NO 14
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
ctttcaccag cgtttctggg tga                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcctgaatgg cgaatggcgc ctg                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggccagtgca cgtctgctgt c                                                21

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggatttgtc ctactcagga gagcg                                            25

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggatggcaag atcctggtat ccaccttagc                                       30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctaaggtgg ataccaggat cttgccatcc                                       30

<210> SEQ ID NO 20
<211> LENGTH: 30
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 20
ggatggcaag atcctggtat cctccttagc                                          30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 21
gctaaggagg ataccaggat cttgccatcc                                          30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 22
ggatggcaag atcctggtat ccagcttagc                                          30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 23
gctaagctgg ataccaggat cttgccatcc                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 24
ggatggcaag atcctggtat ccacgttagc                                          30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 25
gctaacgtgg ataccaggat cttgccatcc                                          30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ggatggcaag atcctggtat ccaggttagc                                    30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggatggcaag atcctggtag ccaccttagc                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggatggcaag atcctggtat gattcacagc                                    30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gctgtgaatc ataccaggat cttgccatcc                                    30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggatggcaag atcctggtac gattcacagc                                    30

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtaggatgg caagatcctg gtatgatcct gtgc                               34

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcacaggatc ataccaggat cttgccatcc tacc                               34

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcacaccatc ataccaggat cttgccatcc tacc                               34

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
taagaaacca ttattatcat gacattaac                                     29

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgatgtata ccaggatctt g                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atagtgtata ccaggatctt g                                             21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ataatgtata ccaggatctt g                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 38
atgctgtata ccaggatctt g                                          21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atcgtgtata ccaggatctt g                                          21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atcctgtata ccaggatctt g                                          21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atggtgtcta ccaggatctt g                                          21

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtaggatgg caagatcctg gtatac                                     26

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gacgtcaggt ggcactttt                                             19

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtaggatgg caagatcctg atatacacc                                29

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggtaggatgg caagattctg gtatacacc                                29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtaagatgg caagatcctg gtatacacc                                29

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtaaaatgg caagatcctg gtata                                    25

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ataggaggta ggatggcaag atcctgg                                  27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaacccagga tcttgccatc ctacctc                                  27

<210> SEQ ID NO 50
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50 augcuggga gccugucuca aucccccggc uaaaaugg         38

<210> SEQ ID NO 51
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 51
uugcgaucag agcggcgcga uguauacucg cagcgagaca ggcuaccuag caagaccccu         60 ucguggguc gcauucuuca cccccucgca gcagcgaggg gguucguuu                     109

<210> SEQ ID NO 52
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 52
ggauggcaag auccugguau gcuggggagc cugaaaaggc uaccuagcaa gaccccuucg         60
uggggucgca uucuucaccc ccucgcagca gcgaggggu uc                            102

<210> SEQ ID NO 53
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 53
gguggcugag aucagccacu ucgcugggga gccugaaaag gcuaccagc aagacccuu          60 cguggggucg cauucuucac ccccucgcag cagcgagggg guuc                         104

<210> SEQ ID NO 54
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 54
gguaggaugg caagauccug guaugcuggg gagccugaaa aggcuaccua gcaagacccc         60 uucgugggu cgcauucuuc accccucgc agcagcgagg ggguuc                         106

<210> SEQ ID NO 55
<211> LENGTH: 108
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 55
ggcggcagua gcgcgguggu cccaccgcug gggagccuga aaaggcuacc uagcaagacc         60
ccuucguggg gucgcauucu ucaccccccuc gcagcagcga gggguuc                     108

<210> SEQ ID NO 56

<211> LENGTH: 30
<212> TYPE: DNA
<213> ORGANISM: Unknown
<220> FEATURE:
<223> OTHER INFORMATION: Description of Unknown:
      Target sequence

<400> SEQUENCE: 56
ggatggcaag atcctggtat ccaccttagc                                   30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggatggcaag atcctggtat cctccttagc                                   30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggatggcaag atcctggtat ccagcttagc                                   30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggatggcaag atcctggtat ccacgttagc                                   30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggatggcaag atcctggtat ccaccttagc                                   30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gctgtgaatc ataccaggat cttgccatcc                                   30

<210> SEQ ID NO 62
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggatggcaag atcctggtat gattcacagc                                          30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggatggcaag atcctggtat ccaggttagc                                          30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gctaaggtgg ataccaggat cttgccatcc                                          30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggatggcaag atcctggtat ccaccttagc                                          30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gctaacctgg ataccaggat cttgccatcc                                          30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggatggcaag atcctggtat ccaccttagc                                          30

<210> SEQ ID NO 68
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 68
ggatggcaag atcctggtat gattcttagc                                       30

<210> SEQ ID NO 69
<211> LENGTH: 11
<212> TYPE: DNA
<213> ORGANISM: Unknown
<220> FEATURE:
<223> OTHER INFORMATION: Description of Unknown:
      Plasmid substrate sequence

<400> SEQUENCE: 69
ggtatacacc a                                                           11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggtatacatc a                                                           11

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggtatacact a                                                           11

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggtatacatt a                                                           11

<210> SEQ ID NO 73
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggtatacagc a                                                           11

<210> SEQ ID NO 74
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 74
ggtatacacg a                                                              11

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggtatacagg a                                                              11

<210> SEQ ID NO 76
<211> LENGTH: 15
<212> TYPE: DNA
<213> ORGANISM: Unknown
<220> FEATURE:
<223> OTHER INFORMATION: Description of Unknown:
      Target sequence

<400> SEQUENCE: 76
atcctggtat acacc                                                          15

<210> SEQ ID NO 77
<211> LENGTH: 29
<212> TYPE: DNA
<213> ORGANISM: Unknown
<220> FEATURE:
<223> OTHER INFORMATION: Description of Unknown:
      Plasmid protospacer sequence

<400> SEQUENCE: 77
ggtaggatgg caagatcctg gtatacacc                                           29

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggtaggatgg caagatcctg gtagacacc                                           29

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggtaggatgg caagatcctg atatacacc                                           29

<210> SEQ ID NO 80
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 80
ggtaggatgg caagattctg gtatacacc                                          29

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggtaagatgg caagatcctg gtatacacc                                          29

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ggtaaaatgg caagatcctg gtatacacc                                          29

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctcttccgat ctggtattcc ccactaagaa accattatta tcatgacatt aacctataaa        60

<210> SEQ ID NO 84
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctcttccgat cttataccccc cgtaagaaac cattattatc atgacattaa cctataaa        58

<210> SEQ ID NO 85
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctcttccgat cttataccccc cgtaagaaac cattattatc atgacattaa cctataaa        58

<210> SEQ ID NO 86
<211> LENGTH: 58
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 86
ctcttccgat cttatacccc cgtaagaaac cattattatc atgacattaa cctataaa    58

<210> SEQ ID NO 87
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctcttccgat cttatacacc cctaagaaac cattattatc atgacattaa cctataaa    58

<210> SEQ ID NO 88
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctcttccgat cttatacacc cctaagaaac cattattatc atgacattaa cctataaa    58

<210> SEQ ID NO 89
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctcttccgat cttatacacc cctaagaaac cattattatc atgacattaa cctataaa    58

<210> SEQ ID NO 90
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctcttccgat cttatacacc cctaagaaac cattattatc atgacattaa cctataaa    58

<210> SEQ ID NO 91
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctcttccgat cttattagcc cctaagaaac cattattatc atgacattaa cctataaa    58

<210> SEQ ID NO 92
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 92
ctcttccgat cttatttccc agtaagaaac cattattatc atgacattaa cctataaa      58

<210> SEQ ID NO 93
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ctcttccgat cttattaccc agtaagaaac cattattatc atgacattaa cctataaa      58

<210> SEQ ID NO 94
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctcttccgat cttattcccc actaagaaac cattattatc atgacattaa cctataaa      58

<210> SEQ ID NO 95
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctcttccgat cttatcaacc cataagaaac cattattatc atgacattaa cctataaa      58

<210> SEQ ID NO 96
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctcttccgat cttatctacc tataagaaac cattattatc atgacattaa cctataaa      58

<210> SEQ ID NO 97
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctcttccgat cttatccacc tttaagaaac cattattatc atgacattaa cctataaa      58

<210> SEQ ID NO 98
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 98
ctcttccgat cttatccacc tttaagaaac cattattatc atgacattaa cctataaa         58

<210> SEQ ID NO 99
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ctcttccgat cttatccccc attaagaaac cattattatc atgacattaa cctataaa         58

<210> SEQ ID NO 100
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctcttccgat cttatccccc attaagaaac cattattatc atgacattaa cctataaa         58

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggtaggatgg caagatcctg gtatgatcct gtgc                                   34

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggtaggatgg caagatcctg gtatgatcct gtgc                                   34

<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcacaccatc ataccaggat cttgccatcc tacc                                   34
```